United States Patent
Prasad et al.

(10) Patent No.: US 10,493,209 B2
(45) Date of Patent: Dec. 3, 2019

(54) LEAK-FREE STOPPER HAVING LOW BREAKLOOSE AND SUSTAINING FORCES

(71) Applicant: Becton, Dickinson and Company, Franklin Lakes, NJ (US)

(72) Inventors: Shishir Prasad, Ridgewood, NJ (US); Gheorghe Cojocariu, Bridgewater, NJ (US); Sathya Kaliyamoorthy, Morris Plains, NJ (US); Chad Smith, Oak Ridge, NJ (US); Ankur Kulshrestha, Hillsborough, NJ (US); Richard G. Giddes, Edison, NJ (US); Gerald Bonczynski, Columbus, NE (US); Kweku Addae-Mensah, Hackensack, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 792 days.

(21) Appl. No.: 14/525,395

(22) Filed: Oct. 28, 2014

(65) Prior Publication Data

US 2015/0119817 A1 Apr. 30, 2015

Related U.S. Application Data

(60) Provisional application No. 61/896,332, filed on Oct. 28, 2013.

(51) Int. Cl.
*C08L 53/00* (2006.01)
*A61M 5/315* (2006.01)
(Continued)

(52) U.S. Cl.
CPC ...... *A61M 5/31513* (2013.01); *A61M 5/3134* (2013.01); *C08K 5/20* (2013.01);
(Continued)

(58) Field of Classification Search
CPC .... A61M 5/31513; C08L 27/18; C08L 53/00; C08L 53/02; C08L 23/06
See application file for complete search history.

(56) References Cited

U.S. PATENT DOCUMENTS

| 4,080,357 A | 3/1978 | Gergen et al. |
| 5,632,733 A | 5/1997 | Shaw |

(Continued)

FOREIGN PATENT DOCUMENTS

| EP | 0264273 A2 | 4/1988 |
| EP | 0686486 A2 | 12/1995 |

(Continued)

OTHER PUBLICATIONS

Holden, "Elastomers, Thermoplastic", Encyclopedia of Polymer Science and Engineering, 1986, pp. 416-418, vol. 5, John Wiley & Sons.

(Continued)

*Primary Examiner* — Mark S Kaucher
(74) *Attorney, Agent, or Firm* — The Webb Law Firm

(57) ABSTRACT

A thermoplastic elastomer stopper that meets the desired material properties of a stopper for a syringe assembly is disclosed. The compression set of the thermoplastic elastomer stopper of the present disclosure is ≤50% when measured at 25% compression for 22 hrs at 70 degree C. The hardness of the thermoplastic elastomer stopper of the present disclosure is 40-70 Shore A. The viscosity of a thermoplastic elastomer stopper of the present disclosure is ≥70 Pa·s at 1,000 $s^{-1}$ shear rate, ≥12.0 Pa·s at 10,000 $s^{-1}$ shear rate, and ≥3.0 Pa·s at 50,000 $s^{-1}$ shear rate when measured using a capillary rheometer at 205 degree C. (Die: Roundhole 20 mm length/1 mm diameter/180 degree inlet, Piston: d=15 mm, and melting time=7 min). The present (Continued)

non-lubricated stopper exhibits the required functional performance of a lubricated stopper.

23 Claims, 22 Drawing Sheets

(51) Int. Cl.
*C08K 5/20* (2006.01)
*C08L 23/06* (2006.01)
*A61M 5/31* (2006.01)
*C08L 27/18* (2006.01)
*C08L 53/02* (2006.01)

(52) U.S. Cl.
CPC ............ *C08L 23/06* (2013.01); *C08L 27/18* (2013.01); *C08L 53/00* (2013.01); *C08L 53/025* (2013.01); *A61M 2005/3101* (2013.01); *C08L 2203/02* (2013.01); *C08L 2205/03* (2013.01)

(56) References Cited

U.S. PATENT DOCUMENTS

| | | | |
|---|---|---|---|
| 7,943,242 B2 | 5/2011 | Liu et al. | |
| 8,075,995 B2 | 12/2011 | Zhao et al. | |
| 2002/0016410 A1 | 2/2002 | Katayama et al. | |
| 2004/0084852 A1 | 5/2004 | Tachikawa et al. | |
| 2007/0000926 A1* | 1/2007 | Jacob | C08L 23/22 220/233 |
| 2007/0142554 A1 | 6/2007 | Ellul et al. | |
| 2009/0062445 A1* | 3/2009 | Moritani | C08K 5/10 524/315 |
| 2010/0243292 A1* | 9/2010 | Telley | H01B 13/0023 174/117 F |
| 2010/0267899 A1* | 10/2010 | Nakano | C08L 23/10 525/194 |
| 2011/0137263 A1 | 6/2011 | Ashmead et al. | |
| 2017/0274679 A1* | 9/2017 | Nitta | B65H 5/06 |

FOREIGN PATENT DOCUMENTS

| | | |
|---|---|---|
| EP | 0879611 A2 | 11/1998 |
| EP | 1028141 A1 | 8/2000 |
| EP | 1566405 A1 | 8/2005 |
| EP | 1739127 A1 | 1/2007 |
| EP | 2208753 A1 | 7/2010 |
| JP | 11255978 A | 9/1999 |
| JP | 2001145697 A | 5/2001 |
| JP | 200289717 A | 3/2002 |
| JP | 2006314824 A | 11/2006 |
| JP | 2009534152 A | 9/2009 |
| WO | 2009044790 A1 | 4/2009 |
| WO | 2012/044744 A1 | 4/2012 |
| WO | 2013057119 A1 | 4/2013 |

OTHER PUBLICATIONS

"Crodamide: Fatty Acid Amides", Crodamide brochure (Jun. 2005).
"Crodamide slip & anti-block for easier processing & handling of polyolefins", Croda Polymer Additives brochure (2008).
Llop et al. "Control of the Migration Behavior of Slip Agents in Polyolefin-based Films", Polymer Engineering and Science 2011, pp. 1763-1769.
"Slip Masterbatches & Concentrates", Ampacet Corporation website http://www.ampacet.com/masterbatch-products/slip-concentrates/.
Wypych, "Handbook of Antiblocking, Release, and Slip Additives" (book), pp. 102-104. ChemTec Publishing, Jan. 2005 Online Google Books web address http://books.google.com/books?id=JmqTzfPZ9QIC&pg=PA103&lpg=PA103&dq=erucamide+friction+tpe&source=bl&ots=PUHrn9_a1F&sig=rgvt4wkJp-jOekQ1CiOVW-gm8Ck&hl=en&sa=X&ei=cZROVJT6Ncq6ggS3-oLABA&ved=0CCAQ6AEwAg#v=onepage&q=erucarnide%20friction%20tpe&f=false.
Grueninger, "Elastomeric Components for Prefilled Syringes", Helvoet Pharma, 2011, pp. 1-4.
"BD Plunger Stoppers", 2016. pp. 1-3.
Robert Shanks and Ing Kong (2012). Thermoplastic Elastomers, Thermoplastic Elastomers, Prof. Adel El-Sonbati (Ed.), ISBN: 978-953-51-0346-2, InTech, pp. 137-154 Available from: http://www.intechopen.com/books/thermoplastic-elastomers/thermoplastic-elastomers.
"Evoprene G Thermoplastic Elastomer (TPE) Compounds", AlphaGary, 2007, pp. 1-2.
PolyOne. "Injection Molding: Part Design", 2013. http://www.polyone.com/products/thermoplastic-elastomers/tpe-knowledge-center/injection-molding-guide/injection-molding-2.
"Evoprene GC Thermoplastic Elastomer (TPE) Compounds", AlphaGary, 2007, pp. 1-2.
"Injection Moulding Guide", AlphaGary, 2007, pp. 1-4.
"Evoprene Thermoplastic Elastomer (TPE) Compounds—General Information", AlphaGary, 2007, pp. 1-4.
"Evoprene Super G Thermoplastic Elastomer (TPE) Compounds", AlphaGary, 2007, pp. 1-2.

* cited by examiner

| STRAIN | DESIRED STRESS (psi) | TPE-1 STRESS (psi) | TPE-2 STRESS (psi) | TPE-3 STRESS (psi) |
|---|---|---|---|---|
| -25% | -143 | -809 | -1147 | -314 |
| -10% | -50 | -170 | -235 | -80 |
| 10% | 45 | 85 | 110 | 48 |
| 25% | 94 | 142 | 90 | 91 |

FIG.11

| TPE/RUBBER IN 10 ml, GAMMA STERILE, T=0 | LEAK PRESSURE (psi), AVG/ST DEV, IT1499-01 | BREAK-LOOSE FORCE (lbf), AVG/ST DEV, IT16-01 | BREAK-OUT FORCE (lbf), AVG/ST DEV, IT16-01 | SUSTAINING FORCE (lbf), AVG/ST DEV, IT16-01 |
|---|---|---|---|---|
| CONVENTIONAL RUBBER DESIGN 1 | 189.0/29.9 | 3.9/0.6 | 1.2/0.2 | 0.9/0.1 |
| TPE-1 STOPPER, DESIGN 2 | 102.9/10.3 | 5.8/0.6 | 1.5/0.2 | 1.0/0.1 |
| TPE-1 STOPPER, DESIGN 3 | 204.0/14.3 | 3.5/0.5 | 0.9/0.1 | 0.5/0.1 |

FIG.12

| TPE, GAMMA STERILE SYRINGE, 10ml DESIGN-4, T=0 | BREAK-LOOSE FORCE (lbf), AVG/ST DEV, IT16-01 | BREAK-OUT FORCE (lbf), AVG/ST DEV, IT16-01 | SUSTAINING FORCE (lbf), AVG/ST DEV, IT16-01 |
|---|---|---|---|
| TPE-1-S0.6, LUBED STOPPER | 3.5/0.5 | 0.9/0.1 | 0.5/0.1 |
| TPE-1-S0.6, UNLUBED STOPPER | 3.3/0.7 | 0.9/0.1 | 0.5/0.1 |
| TPE-2-S0.6, LUBED STOPPER | 3.2/0.5 | 0.8/0.1 | 0.8/0.1 |
| TPE-2-S0.6, UNLUBED STOPPER | 3.8/0.4 | 0.7/0.1 | 0.5/0.1 |

FIG.13

| TPE STOPPER IN DESIGN-5, 10ml SYRINGE, UNLUBED STOPPER, NON-STERILE SYRINGE, NO NEEDLE ATTACHED | ISOPROPANOL HAND CONTROL | SHEEP BLOOD HAND CONTROL |
|---|---|---|
| TPE-1 | GOOD CONTROL AT DROPLET LEVEL | GOOD CONTROL AT DROPLET LEVEL |
| TPE-2 | GOOD CONTROL AT DROPLET LEVEL | GOOD CONTROL AT DROPLET LEVEL |
| TPE-4 | BAD CONTROL WITH SPURTING | BAD CONTROL WITH SPURTING |
| TPE-5 | BAD CONTROL WITH SPURTING | BAD CONTROL WITH SPURTING |

FIG.14B

| 10ml SYRINGE, NON-STERILE | FLUID PRESSURE (psi) | CONTACT PRESSURE USING FINITE ELEMENT ANALYSIS (psi) | NORMALIZED CONTACT PRESSURE USING FINITE ELEMENT ANALYSIS (psi) |
|---|---|---|---|
| STOPPER DESIGN-1, CONVENTIONAL RUBBER-2 | 0 | 104 | 1 |
| | 67 | 139 | 1.34 |
| | 133 | 38 | 0.37 |
| STOPPER DESIGN-3, TPE-1 | 0 | 206 | 1 |
| | 67 | 383 | 1.86 |
| | 133 | 435 | 2.11 |

FIG.15

| TPE STOPPER CANDIDATE | DESCRIPTION |
|---|---|
| TPE-1-S0.6 | OLEFIN BLOCK COPOLYMER BASED WITH SMALL AMOUNT OF POLYPROPYLENE AS COLORANT CARRIER. CONTAINS 0.6% OF ERUCAMIDE SLIP AGENT |
| TPE-2-S0 | POLYETHYLENE BLENDED WITH STYRENIC BLOCK COPOLYMER BASED WITH SMALL AMOUNT OF POLYPROPYLENE AS COLORANT CARRIER. CONTAINS DIFFERENT LEVEL OF ERUCAMIDE SLIP AGENT (0%, 0.1%, 0.2%, 0.3%, AND 0.6%) |
| TPE-2-S0.1 | |
| TPE-2-S0.2 | |
| TPE-2-S0.3 | |
| TPE-2-S0.6 | |
| TPE-3 | POLYETHYLENE BLENDED WITH STYRENIC BLOCK COPOLYMER BASED WITH SMALL AMOUNT OF POLYPROPYLENE AS COLORANT CARRIER AND HAVING A SECOND COMPOSITION |
| TPE-4 | POLYPROPYLENE BLENDED WITH STYRENIC BLOCK COPOLYMER BASED AND OF LOWER VISCOSITY THAN TPE-1 AND TPE-2 |
| TPE-5 | POLYETHYLENE BLENDED WITH STYRENIC BLOCK COPOLYMER BASED |
| TPE-6 | POLYETHYLENE BLENDED WITH STYRENIC BLOCK COPOLYMER BASED HAVING A SECOND COMPOSITION |
| TPE-7 | OLEFIN BLOCK COPOLYMER FROM DOW (GRADE: 9807) |
| TPE-8 | OLEFIN BLOCK COPOLYMER FROM DOW (GRADE: 9507) |
| TPE-9 | OLEFIN BLOCK COPOLYMER FROM DOW (GRADE: 9817) |
| TPE-10 | POLYETHYLENE BLENDED WITH EPDM TPV PRODUCED WITH POLYPROPYLENE AS CONTINUOUS PHASE |
| TPE-11 | POLYETHYLENE BLENDED WITH EPDM TPV PRODUCED WITH POLYPROPYLENE AS CONTINUOUS PHASE AND HAVING A SECOND COMPOSITION |
| TPE-12 | POLYETHYLENE BLENDED WITH EPDM TPV PRODUCED WITH POLYPROPYLENE AS CONTINUOUS PHASE AND HAVING A THIRD COMPOSITION |
| TPE-13 | POLYPROPYLENE AND POLYETHYLENE BLENDED WITH STYRENIC BLOCK COPOLYMER |
| TPE-14 | POLYPROPYLENE BLENDED WITH STYRENIC BLOCK COPOLYMER BASED HAVING A SECOND COMPOSITION |
| TPE-15 | POLYPROPYLENE BLENDED WITH STYRENIC BLOCK COPOLYMER BASED HAVING A THIRD COMPOSITION |

FIG.16

| TPE STOPPER MATERIAL | PP CONTENT (%) | STICK-SLIP PERFORMANCE (PASS/FAIL) |
|---|---|---|
| TPE-1 | <1 | PASS (0/5 SYRINGE EXHIBIT STICK-SLIP) |
| TPE-2-S0 | <1 | PASS (0/5 SYRINGE EXHIBIT STICK-SLIP) |
| TPE-2-S0.1 | | PASS (0/5 SYRINGE EXHIBIT STICK-SLIP) |
| TPE-2-S0.2 | | PASS (0/5 SYRINGE EXHIBIT STICK-SLIP) |
| TPE-2-S0.3 | | PASS (0/5 SYRINGE EXHIBIT STICK-SLIP) |
| TPE-2-S0.6 | | PASS (0/5 SYRINGE EXHIBIT STICK-SLIP) |
| TPE-3 | <1 | PASS (0/5 SYRINGE EXHIBIT STICK-SLIP) |
| TPE-4 | 20 | FAIL (5/5 SYRINGES EXHIBIT STICK-SLIP) |
| TPE-5 | <1 | PASS |
| TPE-6 | <1 | FAIL (5/5 SYRINGES EXHIBIT STICK-SLIP) |
| TPE-7 | N/A | PASS (0/5 SYRINGE EXHIBIT STICK-SLIP) |
| TPE-8 | N/A | PASS (0/5 SYRINGE EXHIBIT STICK-SLIP) |
| TPE-9 | N/A | PASS (0/5 SYRINGE EXHIBIT STICK-SLIP) |
| TPE-10 | 1.03 | FAIL (1/5 SYRINGE EXHIBIT STICK-SLIP) |
| TPE-11 | 1.14 | FAIL (2/5 SYRINGES EXHIBIT STICK-SLIP) |
| TPE-12 | 1.19 | FAIL (2/5 SYRINGES EXHIBIT STICK-SLIP) |
| TPE-13 | 1.90 | FAIL (3/5 SYRINGES EXHIBIT STICK-SLIP) |
| TPE-14 | 5.66 | FAIL (3/3 SYRINGES EXHIBIT STICK-SLIP) |
| TPE-15 | 7.91 | FAIL (5/5 SYRINGES EXHIBIT STICK-SLIP) |

FIG.17

| STOPPER MATERIAL | PP CONTENT (%) | POLYETHYLENE CONTENT (%) | COMPRESSION SET (%) | LEAK PERFORMANCE (PASS/FAIL ISO7886-1 REQUIREMENT) |
|---|---|---|---|---|
| TPE-1-S0.6 | <1 | N/A | 29 | PASS |
| TPE-2-S0 | <1 | 25.7 | 20 | PASS |
| TPE-2-S0.1 | | | | PASS |
| TPE-2-S0.2 | | | | PASS |
| TPE-2-S0.3 | | | | PASS |
| TPE-2-S0.6 | | | | PASS |
| TPE-3 | <1 | NOT EVALUATED BASED ON THE STRESS AT GIVEN STRAIN (DISCUSSED LATER) | | |
| TPE-4 | 20 | | | |
| TPE-5 | <1 | 24.8 | 35 | PASS |
| TPE-6 | <1 | 7.6 | | |
| TPE-7 | N/A | N/A | 76 | FAIL |
| TPE-8 | N/A | N/A | 61 | FAIL |
| TPE-9 | N/A | N/A | 58 | FAIL |
| TPE-10 | 1.03 | | | |
| TPE-11 | 1.14 | | | |
| TPE-12 | 1.19 | | | |
| TPE-13 | 1.9 | | | |
| TPE-14 | 5.66 | | | |
| TPE-15 | 7.91 | | | |

FIG.20

| STOPPER MATERIAL | PP CONTENT (%) | POLYETHYLENE CONTENT (%) | COMPRESSION SET (%) | VISCOSITY (Pa.s) | | | SHEEP BLOOD HAND CONTROL | ISOPROPANOL HAND CONTROL |
|---|---|---|---|---|---|---|---|---|
| | | | | SHEAR RATE= 1000/S | SHEAR RATE= 10000/S | SHEAR RATE= 50000/S | | |
| TPE-1-S0.6 | <1 | N/A | 29 | 163.9 | 29.1 | 7.1 | PASS | PASS |
| TPE-2-S0 | | | | | | | PASS | FAIL |
| TPE-2-S0.1 | | 25.7 | 20 | 91.3 | 17.3 | 5.4 | PASS | FAIL |
| TPE-2-S0.2 | <1 | | | | | | PASS | FAIL |
| TPE-2-S0.3 | | | | | | | PASS | PASS |
| TPE-2-S0.6 | | | | | | | PASS | PASS |
| TPE-3 | <1 | NOT EVALUATED BASED ON THE STRESS AT GIVEN STRAIN (DISCUSSED LATER) | | | | | | |
| TPE-4 | 20 | | | | | | | |
| TPE-5 | <1 | 24.8 | 35 | 70.5 | 9.9 | 2.5 | FAIL | FAIL |
| TPE-6 | <1 | 7.6 | 69.45 | | 12.39 | 3.72 | FAIL | FAIL |
| TPE-7 | N/A | N/A | 76 | | | | | |
| TPE-8 | N/A | N/A | 61 | | | | | |
| TPE-9 | N/A | N/A | 58 | | | | | |
| TPE-10 | 1.03 | | | | | | | |
| TPE-11 | 1.14 | | | | | | | |
| TPE-12 | 1.19 | | | | | | | |
| TPE-13 | 1.9 | | | | | | | |
| TPE-14 | 5.66 | | | | | | | |
| TPE-15 | 7.91 | | | | | | | |

FIG.21

| TPE-2 WITH DIFFERENT ERUCAMIDE LEVEL, UNLUBED STOPPER | BREAK-LOOSE FORCE (lbf), AVG/ST DEV, IT16-01 (SPEED: 1150 ml/hr) | BREAK-OUT FORCE (lbf), AVG/ST DEV, IT16-01 (SPEED: 1150 ml/hr) | SUSTAINING FORCE (lbf), AVG/ST DEV, IT16-01 (SPEED: 1150 ml/hr) | PUMP FORCE (lbf), AVG/ST DEV, IT1687-02 (SPEED: 10 ml/hr) |
|---|---|---|---|---|
| 0% | 3.07/0.17 | 0.8/0.19 | 0.45/0.11 | 2.17/0.31 |
| 0.1% | 3.05/0.17 | 0.73/0.20 | 0.44/0.08 | 1.76/0.15 |
| 0.2% | 2.92/0.14 | 0.59/0.35 | 0.35/0.11 | 1.51/0.24 |
| 0.3% | 2.89/0.17 | 0.50/0.19 | 0.34/0.08 | 1.25/0.18 |

FIG.22

| TPE | LEAK PRESSURE RANKING | SUSTAINING FORCE RANKING |
|---|---|---|
| TPE-1-S0.6 | 2 | 2 |
| TPE-2-S0.6 | 1 | 3 |
| TPE-3 | 3 | 1 |

FIG.23

| TPE | LEAK PRESSURE (psi), AVG/ST DEV, IT1499-01 | SUSTAINING FORCE (lbf), AVG/ST DEV, IT16-01 |
|---|---|---|
| TPE-1-S0.6 | 227.4/35.4 | 1.03/0.09 |
| TPE-2-S0.6 | 245.3/32.5 | 1.14/0.05 |
| TPE-3 | 121.8/17.7 | 0.73/0.08 |

| STOPPER MATERIAL | PP CONTENT (%) | POLYETHYLENE CONTENT (%) | COMPRESSION SET (%) | VISCOSITY (Pa.s) SHEAR RATE= 1000/S | VISCOSITY (Pa.s) SHEAR RATE= 10000/S | VISCOSITY (Pa.s) SHEAR RATE= 50000/S | SHEEP BLOOD HAND CONTROL | ISOPROPANOL HAND CONTROL | STRESS AT GIVEN STRAIN |
|---|---|---|---|---|---|---|---|---|---|
| TPE-1-S0.6 | <1 | N/A | 29 | 163.9 | 29.1 | 7.1 | PASS | PASS | PASS |
| TPE-2-S0 | | | | | | | PASS | FAIL | |
| TPE-2-S0.1 | <1 | 25.7 | 20 | 91.3 | 17.3 | 5.4 | PASS | FAIL | |
| TPE-2-S0.3 | | | | | | | PASS | PASS | PASS |
| TPE-2-S0.6 | | | | | | | PASS | PASS | PASS |
| TPE-3 | <1 | | NOT EVALUATED BASED ON THE STRESS AT GIVEN STRAIN | | | | | | FAIL |
| TPE-4 | 20 | | | 70.5 | 9.9 | 2.5 | FAIL | FAIL | |
| TPE-5 | <1 | 24.8 | 35 | 69.45 | 12.39 | 3.72 | FAIL | FAIL | |
| TPE-6 | <1 | 7.6 | | | | | | | |
| TPE-7 | N/A | N/A | 76 | | | | | | |
| TPE-8 | N/A | N/A | 61 | | | | | | |
| TPE-9 | N/A | N/A | 58 | | | | | | |
| TPE-10 | 1.03 | | | | | | | | |
| TPE-11 | 1.14 | | | | | | | | |
| TPE-12 | 1.19 | | | | | | | | |
| TPE-13 | 1.9 | | | | | | | | |
| TPE-14 | 5.66 | | | | | | | | |
| TPE-15 | 7.91 | | | | | | | | |

| TPE STOPPER IN DESIGN-5, 10ml SYRINGE, UNLUBED STOPPER, E-BEAM STERILE SYRINGE, NO NEEDLE ATTACHED, SLIP ADDITIVE (ERUCAMIDE) LEVEL IN TPE-2 (%) | ISOPROPANOL HAND CONTROL | SHEEP BLOOD HAND CONTROL |
|---|---|---|
| 0% | BAD CONTROL WITH SPURTING | GOOD CONTROL AT DROPLET LEVEL |
| 0.1% | BAD CONTROL WITH SPURTING | GOOD CONTROL AT DROPLET LEVEL |
| 0.2% | BAD CONTROL WITH SPURTING | GOOD CONTROL AT DROPLET LEVEL |
| 0.3% | GOOD CONTROL AT DROPLET LEVEL | GOOD CONTROL AT DROPLET LEVEL |

FIG.26

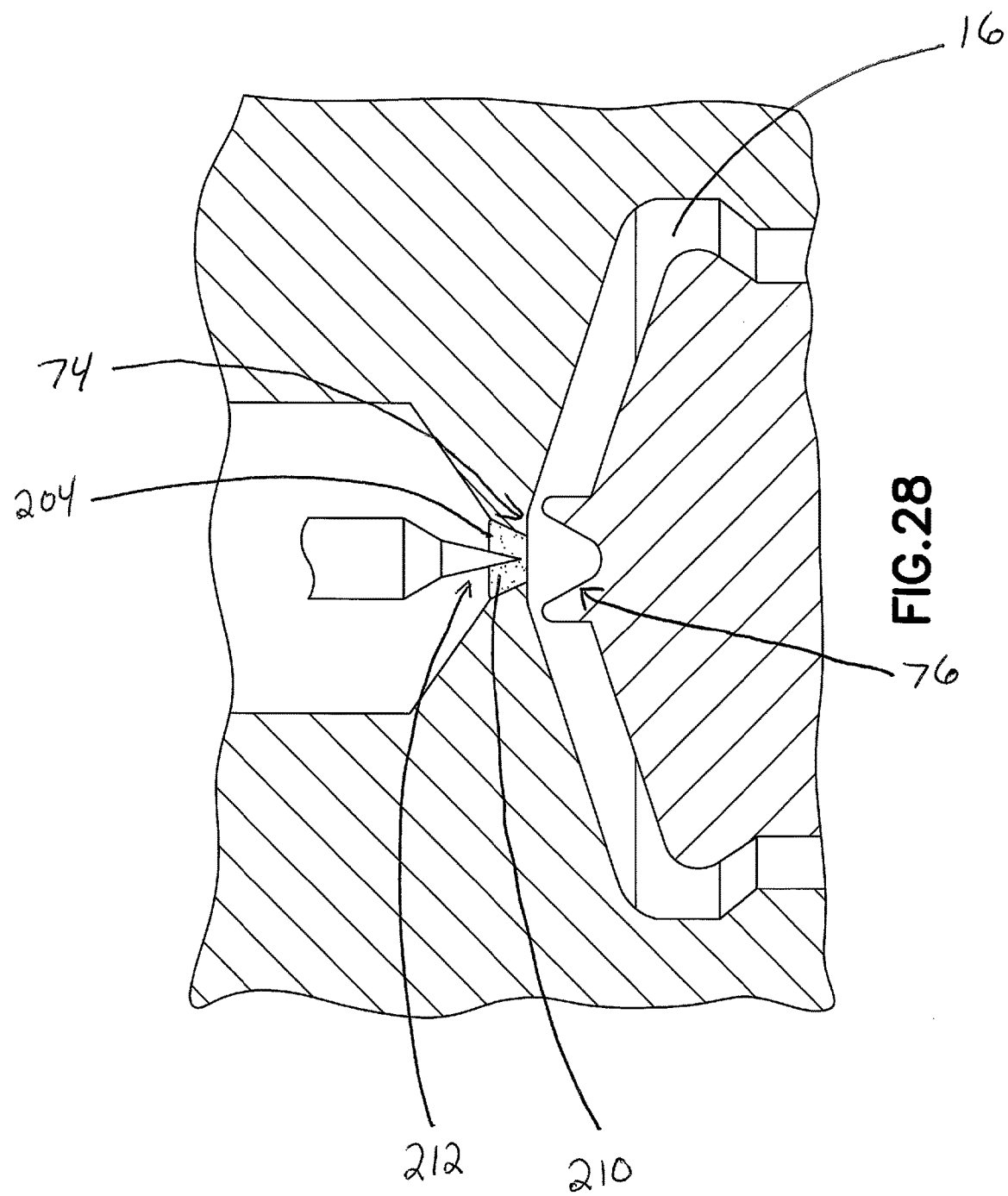

LEAK-FREE STOPPER HAVING LOW BREAKLOOSE AND SUSTAINING FORCES

CROSS-REFERENCE TO RELATED APPLICATIONS

This application claims priority to U.S. Provisional Patent Application Ser. No. 61/896,332, filed Oct. 28, 2013, the entire disclosure of which is hereby expressly incorporated by reference herein.

BACKGROUND OF THE INVENTION

1. Field of the Disclosure

The present disclosure relates generally to a stopper for a syringe assembly. More particularly, the present disclosure relates to a thermoplastic elastomer (TPE) stopper that meets the desired material properties of a stopper for a syringe assembly.

2. Description of the Related Art

Syringe assemblies are well known in the medical field for dispensing fluids, such as medications. A conventional syringe typically includes a syringe barrel with an opening at one end and a plunger mechanism disposed through the opposite end. The plunger mechanism typically includes a plunger rod extending through the barrel, with a plunger head or stopper disposed at the end of the plunger rod within the syringe barrel, and with a finger flange at the other end of the plunger rod extending out of the syringe barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the syringe barrel for attachment with a fluid line of a patient. Upon the user applying a force to depress the plunger rod and stopper through the syringe barrel towards the front end of the syringe barrel, the contents of the syringe are thereby forced out of the syringe barrel through the opening at the front end for delivery to the patient. Such an operation is well known in the medical field, and medical practitioners have become well accustomed to the use of such common fluid delivery procedures through standard syringes.

Syringe assemblies require slow and controlled initiation and maintenance of sliding movement of one surface over another surface. It is well known that two stationary surfaces having a sliding relationship often exhibit sufficient resistance to initiation of movement that gradually increased pressure applied to one of the surfaces does not cause movement until a threshold pressure is reached, at which point a sudden sliding separation of the surfaces takes place. This sudden separation of stationary surfaces into a sliding relationship is herein referred to as "breakout".

A less well known, but important frictional force is "breakloose force", which refers to the force required to overcome static friction between surfaces of a syringe assembly that has been subjected to sterilization (including autoclaving or other processes) and may have a slight deformation in one or both of the contacting surfaces of the syringe assembly, for example in the syringe barrel. In addition to autoclaving, parking of the assembly can further increase the breakloose force.

Breakout and breakloose forces are particularly troublesome in liquid dispensing devices, such as syringes, used to deliver small, accurately measured quantities of a liquid by smooth incremental line-to-line advancement of one surface over a graduated second surface. The problem is also encountered in devices using stopcocks, such as burets, pipets, addition funnels, and the like where careful dropwise control of flow is desired.

A critical performance requirement of a stopper is achieving high leak pressure, i.e., the ability of a stopper to maintain a leak-free syringe while maintaining low breakloose and sustaining forces.

The problems of excessive breakout and breakloose forces are related to friction. Friction is generally defined as the resisting force that arises when a surface of one substance slides, or tends to slide, over an adjoining surface of itself or another substance. Between surfaces of solids in contact, there may be two kinds of friction: (1) the resistance opposing the force required to start to move one surface over another, conventionally known as static friction, and (2) the resistance opposing the force required to move one surface over another at a variable, fixed, or predetermined speed, conventionally known as kinetic friction.

The force required to overcome static friction and induce breakout is referred to as the "breakout force", and the force required to maintain steady slide of one surface over another after breakout or breakloose is referred to as the "sustaining force". Two main factors contribute to static friction and thus to the breakout or breakloose force. The term "stick" as used herein denotes the tendency of two surfaces in stationary contact to develop a degree of adherence to each other. The term "inertia" is conventionally defined as the indisposition to motion which must be overcome to set a mass in motion. In the context of the present invention, inertia is understood to denote that component of the breakout force which does not involve adherence.

Breakout or breakloose forces, in particular the degree of stick, vary according to the composition of the surfaces. In general, materials having elasticity show greater stick than non-elastic materials, particularly when the surfaces are of similar composition. The length of time that surfaces have been in stationary contact with each other also influences breakout and/or breakloose forces. In the syringe art, the term "parking" denotes storage time, shelf time, or the interval between filling and discharge. Parking generally increases breakout or breakloose force, particularly if the syringe has been refrigerated during parking.

A conventional approach to overcoming breakout has been application of a lubricant to a surface-to-surface interface. Such conventional lubricated stoppers have the disadvantage of being soluble in a variety of fluids, such as vehicles commonly used to dispense medicaments. In addition, these lubricants are subject to air oxidation resulting in viscosity changes and objectionable color development. Further, they are particularly likely to migrate from the surface-to-surface interface. Such lubricant migration is generally thought to be responsible for the increase in breakout force with time in parking.

Additional problems with applying a lubricant to a surface of a stopper is that such a lubrication step requires costs in lubricants and lubing instruments, time and energy to operate and perform the lubrication step, and the stopper must be removed from an automated assembly process to be lubricated.

For these reasons, there is a need for a better syringe assembly system to overcome high breakout and breakloose forces whereby smooth transition of two surfaces from stationary contact into sliding contact can be achieved and there is a need for a stopper that exhibits the required performance characteristics and that does not require the additional lubrication step.

SUMMARY OF THE INVENTION

The present disclosure provides for a thermoplastic elastomer stopper that meets the desired material properties of a stopper for a syringe assembly. These material properties are compression set, hardness, stress at given strain levels, and viscosity at given shear rates. The compression set of a thermoplastic elastomer stopper of the present disclosure may be ≤50% when measured at 25% compression for 22 hrs at 70 degrees C. (ASTM D395-03, Method B). The hardness of a thermoplastic elastomer stopper of the present disclosure may be in the range of 40-70 Shore A (ASTM D2240-05). The stress at desired strain values should also be optimized for the thermoplastic elastomer stopper of the present disclosure so as to obtain good leak and force performance with the assembled syringe. The viscosity of a thermoplastic elastomer stopper of the present disclosure may be ≥70.0 Pa·s at 1,000 $s^{-1}$ shear rate, ≥12.0 Pa·s at 10,000 $s^{-1}$ shear rate, and ≥3.0 Pa·s at 50,000 $s^{-1}$ shear rate when measured using a capillary rheometer at 205 degrees C. (Die: Roundhole 20 mm length/1 mm diameter/180 degree inlet, Piston: d=15 mm, and melting time=7 min). In one embodiment, a thermoplastic elastomer stopper of the present disclosure provides for sticktion-free performance with a polypropylene or polypropylene copolymer based barrel. For example, a stopper of the present disclosure includes a 30-65% elastomer such as but not limited to 30-65% styrene-ethylene-butylene-styrene (SEBS) copolymer blended with 10-35% medium to high density polyethylene (medium to high density with melting temperature in the range of 120 degrees C. to 130 degrees C.), 20-35% commonly available mineral oil along with commonly available radiation stabilizer, antioxidant, and/or processing aid. The molecular weight of the elastomer and polyethylene are selected so as to obtain the desired material properties as described above.

The present disclosure also provides a stopper that maintains a leak-free syringe with low breakloose and sustaining forces. In one embodiment, the present disclosure provides a non-lubricated stopper that exhibits the required functional performance factors for a syringe assembly. Advantageously, the stopper of the present disclosure provides the required functional performance while eliminating the external lubricant application on a stopper. In this manner, the negative consequences of the external lubricant application on a stopper are eliminated. For example, the lubrication step on a stopper requires costs in lubricants and lubing instruments, time and energy to operate and perform the lubrication step, and the stopper must be removed from an automated assembly process to be lubricated. The non-lubricated stopper of the present disclosure also provides a stopper which allows for a complete automation stopper assembly process. Additionally, a stopper of the present disclosure allows for an autoclavable non-lubricated stopper for a syringe assembly by use of a high melting temperature polymer as the hard phase.

The present invention provides a stopper for a syringe assembly having an exterior surface adapted to sealingly engage an inner surface of a chamber of a medical device. The respective surfaces can be in frictional engagement. When used in a medical device, the stopper of the present invention can reduce the force required to achieve breakout, breakloose, and/or sustaining forces, whereby transition of surfaces from stationary contact to sliding contact occurs without a sudden surge. When breakout or breakloose is complete and the surfaces are in sliding contact, they slide smoothly upon application of very low sustaining force. These advantages are achieved without the use of a lubricant being applied to a surface of the stopper. The present invention also provides a stopper which achieves high leak pressure. In this manner, the stopper of the present disclosure maintains a leak-free syringe with low breakloose and sustaining forces. The effect achieved by the stopper of the present disclosure and methods of the present invention can provide the advantages of leak-free, low breakout, low breakloose, and sustaining forces throughout any parking period. When the stopper of the present disclosure is part of a liquid dispensing device such as a syringe assembly, small highly accurate increments of liquid may be dispensed repeatedly without sudden surges. Thus, a syringe assembly including a stopper of the present disclosure can be used to administer a medicament to a patient without the danger of surges whereby accurate control of dosage and greatly enhanced patient safety are realized. This is achieved and maintained after sterilization and over the lifetime of the stopper, e.g., five (5) years.

In accordance with an embodiment of the present invention, a stopper for a syringe assembly includes a thermoplastic elastomer, wherein the compression set of the thermoplastic elastomer is ≤50% when measured at 25% compression for 22 hrs at 70 degrees C., wherein the hardness of the thermoplastic elastomer is approximately 40-70 Shore A, and wherein the viscosity of the thermoplastic elastomer is ≥70.0 Pa·s at 1,000 shear rate, ≥12.0 Pa·s at 10,000 $s^{-1}$ shear rate, and ≥3.0 Pa·s at 50,000 $s^{-1}$ shear rate when measured using a capillary rheometer at 205 degrees C. (Die: Roundhole 20 mm length/1 mm diameter/180 degree inlet, Piston: d=15 mm, and melting time=7 min).

In one configuration, the compression set of the thermoplastic elastomer is approximately ≤35% when measured at 25% compression for 22 hrs at 70 degrees C. In another configuration, the compression set of the thermoplastic elastomer is approximately 10%-35% when measured at 25% compression for 22 hrs at 70 degrees C. In yet another configuration, the hardness of the thermoplastic elastomer is approximately 45-65 Shore A. In one configuration, the hardness of the thermoplastic elastomer is approximately 53-63 Shore A. In another configuration, the viscosity of the thermoplastic elastomer is 70.0 Pa·s-320.0 Pa·s at 1,000 $s^{-1}$ shear rate. In yet another configuration, the viscosity of the thermoplastic elastomer is 100.0 Pa·s-170.0 Pa·s at 1,000 $s^{-1}$ shear rate. In one configuration, the viscosity of the thermoplastic elastomer is 12.0 Pa·s-46.0 Pa·s at 10,000 $s^{-1}$ shear rate. In another configuration, the viscosity of the thermoplastic elastomer is 16.0 Pa·s-27.0 Pa·s at 10,000 $s^{-1}$ shear rate. In yet another configuration, the viscosity of the thermoplastic elastomer is 3.0 Pa·s-12.0 Pa·s at 50,000 $s^{-1}$ shear rate. In one configuration, the viscosity of the thermoplastic elastomer is 4.5 Pa·s-7.5 Pa·s at 50,000 $s^{-1}$ shear rate.

In accordance with another embodiment of the present invention, a syringe assembly includes a syringe barrel having a proximal end, a distal end, and a sidewall extending therebetween and defining a chamber having an interior, the syringe barrel formed of a first material and a stopper slidably disposed within the interior of the chamber of the syringe barrel, the stopper sized relative to the interior of the chamber of the syringe barrel to provide sealing engagement with the sidewall of the syringe barrel, the stopper formed of a second material different than the first material, wherein the second material does not contain more than 4% of the first material and more preferably the second material does not contain more than 1.5% of the first material and still more preferably the second material does not contain more than 1% of the first material. The syringe assembly further includes a plunger rod having a first end engageable with a portion of the stopper.

In accordance with another embodiment of the present invention, a syringe assembly includes a syringe barrel having a proximal end, a distal end, and a sidewall extending therebetween and defining a chamber having an interior and a stopper slidably disposed within the interior of the chamber of the syringe barrel, the stopper sized relative to the interior of the chamber of the syringe barrel to provide sealing engagement with the sidewall of the syringe barrel, the stopper formed of a non-lubricated thermoplastic elastomer. The syringe assembly further includes a plunger rod having a first end engageable with a portion of the stopper.

In one configuration, the stopper includes a polyethylene blended with styrene block copolymer. In another configuration, the stopper includes an olefin block copolymer containing polyethylene blocks. The stopper composition can also include mineral oil, radiation stabilizer, antioxidant, and/or processing aids.

In accordance with another embodiment of the present invention, a syringe assembly includes a syringe barrel having a proximal end, a distal end, and a sidewall extending therebetween and defining a chamber having an interior, the syringe barrel formed of a barrel material. The syringe assembly further includes a stopper including a thermoplastic elastomer, wherein the compression set of the thermoplastic elastomer is ≤50% when measured at 25% compression for 22 hrs at 70 degrees C., wherein the hardness of the thermoplastic elastomer is 40-70 Shore A, and wherein the viscosity of the thermoplastic elastomer is ≥70.0 Pa·s at 1,000 shear rate, ≥12.0 Pa·s at 10,000 s$^{-1}$ shear rate, and ≥3.0 Pa·s at 50,000 shear rate, the stopper including a formulation including an elastomeric phase such as but not limited to styrene block copolymer, olefin block copolymer, SBR rubber, or polyisoprene and may have a hard polymer phase such as polyolefin, for example, but not limited to, polyethylene and other higher melting temperature polymer (>170 degrees C.) such as ethylene-tetra-fluoro-ethylene and fluorinated ethylene propylene polymers along with hydrocarbon liquids such as mineral oil and radiation stabilizer, antioxidant, and/or other processing aids, the stopper slidably disposed within the interior of the chamber of the syringe barrel, the stopper sized relative to the interior of the chamber of the syringe barrel to provide sealing engagement with the sidewall of the syringe barrel, the stopper formed of a non-lubricated thermoplastic elastomer. The syringe assembly further includes a plunger rod having a first end engageable with a portion of the stopper, wherein the formulation of the stopper is different than the barrel material, for example, the hard phase for the formulation of the stopper should not be polypropylene based in case of the barrel material being formed of polypropylene or polypropylene based barrels.

In accordance with another embodiment of the present invention, a stopper of the present invention provides advantages relating to manufacturing and/or molding. For example, in one embodiment, a stopper of the present invention includes a shear-feature, i.e., a thin-wall section, at the mold gating point within a mold cavity. The shear-feature of a stopper of the present invention adds shear heat at the mold gate point. In this manner, a stopper of the present invention eliminates cold material from entering the mold cavity, eliminates flow lines and/or weld lines common to stopper molding, eliminates sink marks, improves the control of gate quality, improves the mold cycle time, and eliminates surface and/or visual imperfections.

In accordance with another embodiment of the present invention, a stopper for a syringe assembly includes a lower portion, a roof portion having a first thickness, and a shear element disposed adjacent the roof portion, the shear element having a second thickness, wherein the second thickness of the shear element is less than 52% and greater than 36% of the first thickness of the roof portion.

In one configuration, the second thickness of the shear element is approximately 44% of the first thickness of the roof portion. In another configuration, the stopper includes a catch can element having a receiving volume.

In accordance with another embodiment of the present invention, a stopper for a syringe assembly includes a lower portion; a roof portion; a core portion disposed adjacent the roof portion, the core portion having a semi-ellipsoidal shape; a first sealing rib disposed adjacent the roof portion; and a second sealing rib disposed adjacent the lower portion.

In one configuration, the first sealing rib is configured to provide an increased contact pressure at the first sealing rib as a fluid pressure increases. In one embodiment, a first rib width results into lower breakout and sustaining forces along with acceptable compression set during the syringe shelf life. In another configuration, a slip additive is added to the thermoplastic elastomer.

In accordance with another embodiment of the present invention, a stopper of the present disclosure can be used with an unlubed barrel that has been modified with a slip agent. The slip agent may be a combination of a slow blooming component for long term performance and a fast blooming component which reduces friction properties faster.

In accordance with another embodiment of the present invention, a stopper for a syringe assembly includes a lower portion; a roof portion, the roof portion having a first thickness; a shear element disposed adjacent the roof portion, the shear element having a second thickness, wherein the second thickness of the shear element is less than 52% and greater than 36% of the first thickness of the roof portion; and a catch can element having a receiving volume.

In accordance with another embodiment of the present invention, a syringe assembly includes a syringe barrel having a proximal end, a distal end, and a sidewall extending therebetween and defining a chamber having an interior, the syringe barrel having a barrel material formulation; a stopper comprising a thermoplastic elastomer, wherein the compression set of the thermoplastic elastomer is ≤50% when measured at 25% compression for 22 hrs at 70 degrees C., wherein the hardness of the thermoplastic elastomer is 40-70 Shore A, and wherein the viscosity of the thermoplastic elastomer is ≥70.0 Pa·s at 1,000 s$^{-1}$ shear rate, ≥12.0 Pa·s at 10,000 s$^1$ shear rate, and ≥3.0 Pa·s at 50,000 s$^{-1}$ shear rate, the stopper comprising a formulation having a hard polymer phase having a high melt temperature >170 degrees C., the stopper slidably disposed within the interior of the chamber of the syringe barrel, the stopper sized relative to the interior of the chamber of the syringe barrel to provide sealing engagement with the sidewall of the syringe barrel, the stopper formed of a non-lubricated thermoplastic elastomer; and a plunger rod having a first end engageable with a portion of the stopper, wherein the formulation of the stopper is different than the barrel material formulation.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 11 is a table comparing the stress-strain properties of various stoppers in accordance with an embodiment of the present invention.

FIG. 12 is a table comparing functional properties of various stoppers in accordance with an embodiment of the present invention.

FIG. 13 is a table comparing functional properties of various stoppers in accordance with an embodiment of the present invention.

FIG. 14B is a table of the hand control properties of various stoppers in accordance with an embodiment of the present invention.

FIG. 15 is a table comparing contact pressure values of a conventional stopper with a stopper at a first sealing rib of the stopper in accordance with an embodiment of the present invention.

FIG. 16 is a table of various thermoplastic elastomer stoppers in accordance with an embodiment of the present invention.

FIG. 17 is a table of the polypropylene (PP) content of various thermoplastic elastomer stoppers in accordance with an embodiment of the present invention.

FIG. 20 is a table of the polypropylene (PP) content, polyethylene (PE) content, compression set, and leak performance of various thermoplastic elastomer stoppers in accordance with an embodiment of the present invention.

FIG. 21 is a table of the polypropylene (PP) content, polyethylene content (PE), compression set, viscosity at specific shear rates, and hand controls of various thermoplastic elastomer stoppers in accordance with an embodiment of the present invention.

FIG. 22 is a table of the force performance of a thermoplastic elastomer stopper with different levels of an Erucamide slip agent in accordance with an embodiment of the present invention.

FIG. 23 is a table of the leak pressure and sustaining force rankings for thermoplastic elastomer stoppers as predicted by FEA simulation in accordance with an embodiment of the present invention.

FIG. 24 is a table of the experimental values of leak pressure and sustaining force rankings for thermoplastic elastomer stoppers in accordance with an embodiment of the present invention.

FIG. 25 is a table of material properties for thermoplastic elastomer stoppers in accordance with an embodiment of the present invention.

FIG. 26 is a table of the hand controls of thermoplastic elastomer stoppers with different levels of an Erucamide slip agent in accordance with an embodiment of the present invention.

FIG. 28 is a cross-sectional view of a thermoplastic elastomer stopper and a hot-tip portion of a hot runner system in accordance with an embodiment of the present invention.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
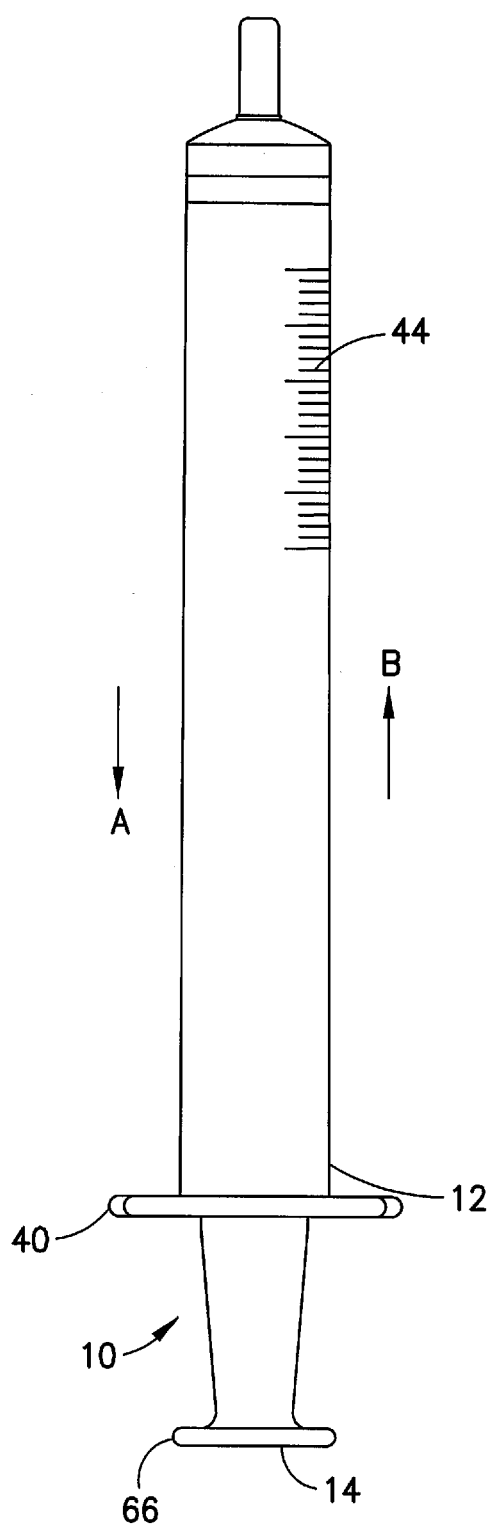
FIG. 1 is an assembled plan view of a syringe assembly including a stopper in a first position in accordance with an embodiment of the present invention.

Other than in the operating examples, or where otherwise indicated, all numbers expressing quantities of ingredients, material properties, and so forth used in the specification and claims and Figures are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values inclusive of the recited values may be used.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a syringe assembly adapted for contact with a patient and/or engagement with a separate device such as a needle assembly or IV connection assembly, and "proximal" refers to the opposite direction of distal, i.e., away from the end of a syringe assembly adapted for engagement with the separate device. For purposes of this disclosure, the above-mentioned references are used in the description of the components of a syringe assembly in accordance with the present disclosure.

The present disclosure provides for a thermoplastic elastomer stopper that meets the desired material properties of a stopper for a syringe assembly. These material properties are compression set, hardness, stress at given strain levels, and viscosity at given shear rates. The compression set of a thermoplastic elastomer stopper of the present disclosure may be ≤50% when measured at 25% compression for 22 Ins at 70 degrees C. (ASTM D395-03, Method B). The hardness of a thermoplastic elastomer stopper of the present disclosure may be in the range of 40-70 Shore A (ASTM D2240-05). The stress at desired strain values should also be optimized for the thermoplastic elastomer stopper of the present disclosure so as to obtain good leak and force performance with the assembled syringe. The viscosity of a thermoplastic elastomer stopper of the present disclosure may be ≥70.0 Pa·s at 1,000 $s^{-1}$ shear rate, ≥12.0 Pa·s at 10,000 $s^{-1}$ shear rate, and ≥3.0 Pa·s at 50,000 $s^{-1}$ shear rate when measured using a capillary rheometer at 205 degrees C. (Die: Roundhole 20 mm length/1 mm diameter/180 degree inlet, Piston: d=15 mm, and melting time=7 min). In one embodiment, a thermoplastic elastomer stopper of the present disclosure provides for sticktion-free performance with a polypropylene or polypropylene copolymer based barrel. For example, a stopper of the present disclosure includes a 30-65% elastomer such as but not limited to 30-65% styrene-ethylene-butylene-styrene (SEBS) copolymer blended with 10-35% medium to high density polyethylene (medium to high density with melting temperature in the range of 120 degree C. to 130 degrees C.), 20-35% commonly available mineral oil along with commonly available radiation stabilizer, antioxidant, and/or processing aids. The molecular weight of the elastomer and polyethylene are selected so as to obtain the desired material properties as described above.

The present disclosure also provides a stopper that maintains a leak-free syringe with low breakloose and sustaining forces. In one embodiment, the present disclosure provides a non-lubricated stopper that exhibits the required functional performance factors for a syringe assembly. Advantageously, the stopper of the present disclosure provides the required functional performance while eliminating the external lubricant application on a stopper. In this manner, the negative consequences of the external lubricant application on a stopper are eliminated. For example, the lubrication step on a stopper requires costs in lubricants and lubing instruments, time and energy to operate and perform the lubrication step, and the stopper must be removed from an automated assembly process to be lubricated. The non-lubricated stopper of the present disclosure also provides a stopper which allows for a complete automation stopper assembly process. Additionally, a stopper of the present disclosure allows for an autoclavable non-lubricated stopper for a syringe assembly by use of a high melting temperature polymer as the hard phase. For example, referring to FIG. 16, multiple different formulations of a stopper of the present disclosure are provided, which are referenced throughout the present disclosure. The formulations include various TPE chemistry such as olefin block copolymer, polyethylene blended with styrenic block copolymer, polypropylene blended with styrenic block copolymer, and polyethylene blended with EPDM TPV. These TPE formulations may contain commonly available radiation stabilizer, antioxidant, and/or processing aids.

In a first exemplary embodiment, a stopper of the present disclosure is formed of an olefin block copolymer, e.g., a TPE-1 embodiment. In a second exemplary embodiment, a stopper of the present disclosure is formed of a polyethylene blended with styrenic block copolymer having a first composition, e.g., a TPE-2 embodiment. In a third exemplary embodiment, a stopper of the present disclosure is formed of a polyethylene blended with styrenic block copolymer having a second composition, e.g., a TPE-3 embodiment. In a fourth exemplary embodiment, a stopper of the present disclosure is formed of a polypropylene blended with styrene block copolymer formulation with a lower viscosity than the TPE-1 and TPE-2 embodiments, e.g., a TPE-4 embodiment. In a fifth exemplary embodiment, a stopper of the present disclosure is formed of a polyethylene blended with styrenic block copolymer having a third composition, e.g., a TPE-5 embodiment. In other exemplary embodiments, a stopper of the present disclosure is formed of other materials and/or formulations, e.g., multiple different exemplary formulations of a stopper of the present disclosure are provided in FIG. 16.

In accordance with another embodiment of the present invention, a stopper of the present disclosure can be used with an unlubricated barrel that has been modified with a slip agent. The slip agent may be a combination of a slow blooming component for long term performance and a fast blooming component which reduces friction properties faster.

Figure 2A:
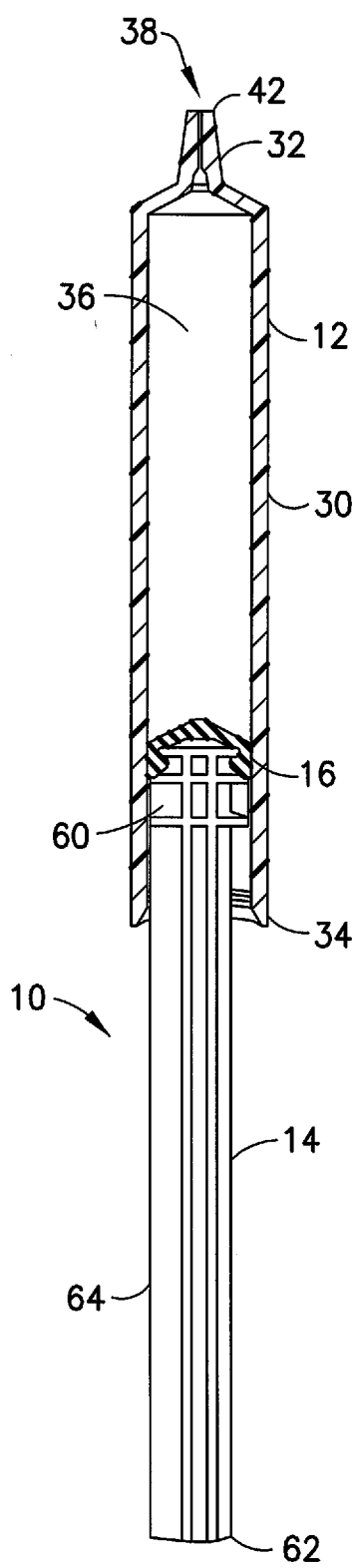
FIG. 2A is a cross-sectional view of the syringe assembly of FIG. 1 with the stopper in a second position in accordance with an embodiment of the present invention.

Referring to FIGS. 1 and 2A, a syringe assembly 10 includes a syringe barrel 12, a plunger rod 14, and a stopper 16. Syringe assembly 10 may be adapted for dispensing and delivery of a fluid and/or collection of a fluid. For example, syringe assembly 10 may be used for injection or infusion of fluid such as a medication into a patient. Syringe assembly 10 is contemplated for use in connection with a needle, such as by connecting syringe assembly 10 to a separate needle assembly (not shown), or alternatively for connection with an intravenous (IV) connection assembly (not shown). It can be appreciated that the present disclosure can be used with any type of syringe assembly. These types of syringes include traditional pre-filled syringe assemblies, metered dose syringes, aspiration syringes for withdrawing fluid from a patient or medication from a container, and the like.

Referring to FIGS. 1 and 2A, syringe barrel 12 generally includes a barrel body or sidewall 30 extending between a first or distal end 32 and a second or proximal end 34. Sidewall 30 defines an elongate aperture or interior chamber 36 of syringe barrel 12. In one embodiment, interior chamber 36 may span the extent of syringe barrel 12 so that syringe barrel 12 is cannulated along its entire length. In one embodiment, syringe barrel 12 may be in the general form of an elongated cylindrical barrel as is known in the art in the general shape of a hypodermic syringe. In alternative embodiments, syringe barrel 12 may be in other forms for containing a fluid for delivery, such as in the general form of an elongated rectangular barrel, for example. Syringe barrel 12 may be formed of glass, or may be injection molded from thermoplastic material such as polypropylene, polyethylene, cycloaliphatic polyolefins, polyesters, or polycarbonate, for example, according to techniques known to those of ordinary skill in the art, though it is to be appreciated that syringe barrel 12 may be made from other suitable materials and according to other applicable techniques. In certain configurations, syringe barrel 12 may include an outwardly extending flange 40 about at least a portion of proximal end 34. Flange 40 may be configured for easy grasping by a medical practitioner.

Distal end 32 of syringe barrel 12 includes outlet opening 38 which is in fluid communication with chamber 36. Outlet opening 38 may be sized and adapted for engagement with a separate device, such as a needle assembly or IV connection assembly and, therefore, may include a mechanism for such engagement as is conventionally known. For example, distal end 32 may include a generally-tapered luer tip 42 for engagement with an optional separate tapered luer structure of such a separate device for attachment therewith (not shown). In one configuration, both the tapered luer tip 42 and the separate tapered luer structure may be provided with syringe assembly 10. In such a configuration, the separate tapered luer structure may be fitted with an attachment mechanism, such as a threaded engagement, for corresponding engagement with a separate device (not shown). In another configuration, tapered luer tip 42 may be provided for direct engagement with a separate device (not shown). In addition, a mechanism for locking engagement therebetween may also be provided with at least one of tapered luer tip 42 and/or the separate tapered luer structure, such as a luer collar or luer lock including interior threads. Such luer connections and luer locking mechanisms are well known in the art.

Proximal end 34 of syringe barrel 12 is generally open-ended, but is intended to be closed off to the external environment as discussed herein. Syringe barrel 12 may also include markings 44, such as graduations located on sidewall 30, for providing an indication as to the level or amount of fluid contained within interior chamber 36 of syringe barrel 12. Such markings 44 may be provided on an external surface of sidewall 30, an internal surface of sidewall 30, or integrally formed or otherwise within sidewall 30 of syringe barrel 12. In other embodiments, alternatively, or in addition thereto, the markings 44 may also provide a description of the contents of the syringe or other identifying information as may be known in the art, such as maximum and/or minimum fill lines.

Syringe assembly 10 may be useful as a pre-filled syringe, and, therefore, may be provided for end use with a fluid, such as a medication or drug, contained within interior chamber 36 of syringe barrel 12, pre-filled by the manufacturer. In this manner, syringe assembly 10 can be manufactured, pre-filled with a medication, and sterilized for delivery, storage, and use by the end user, without the need for the end user to fill the syringe with medication from a separate vial prior to use. In such an embodiment, syringe assembly 10 may include a cap or sealing member disposed at distal end 32 of syringe barrel 12 to seal a fluid, such as a medication, within interior chamber 36 of syringe barrel 12.

Figure 2B:
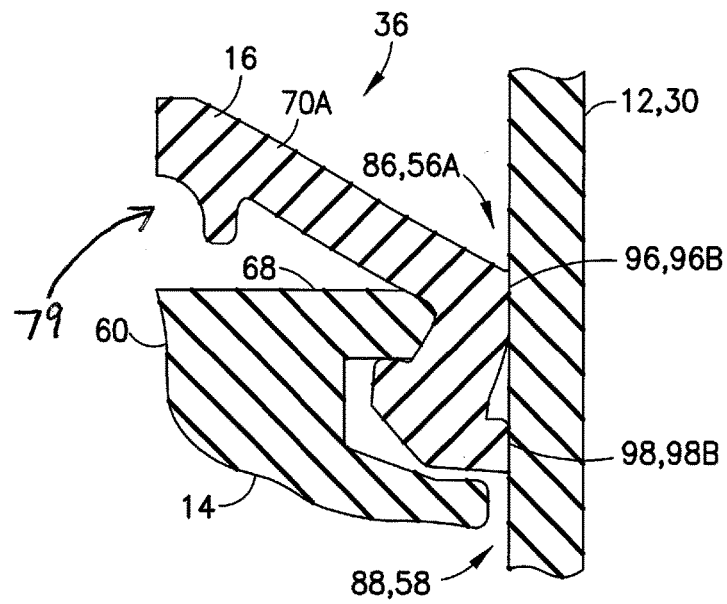
FIG. 2B is a detailed view of a portion of a stopper in contact with an interior surface of a syringe barrel in accordance with an embodiment of the present invention.

Referring to FIGS. 1-2B, syringe assembly 10 includes stopper 16 which is moveably or slidably disposed within interior chamber 36, and is in sealing contact with the internal surface of sidewall 30 of syringe barrel 12. Stopper 16 is sized relative to the interior of syringe barrel 12 to provide sealing engagement with the interior surface of sidewall 30 of syringe barrel 12. In a pre-filled syringe assembly, stopper 16 also provides a seal to prevent liquid or medication from leaking out of syringe barrel 12. Additionally, in one embodiment, stopper 16 may include one or more annular ribs extending around the periphery of stopper 16 to increase the sealing engagement between stopper 16 and the interior surface of sidewall 30 of syringe barrel 12. In alternate embodiments, a singular O-ring or a plurality of O-rings may be circumferentially disposed about stopper 16 to increase the sealing engagement with the interior surface of sidewall 30.

Referring to FIGS. 1 and 2A, syringe assembly 10 further includes plunger rod 14 which provides a mechanism for dispensing fluid contained within interior chamber 36 of syringe barrel 12 through outlet opening 38. Plunger rod 14 is adapted for advancing stopper 16. In one embodiment, plunger rod 14 is sized for movement within interior chamber 36 of syringe barrel 12 as will be discussed in more detail below, and generally includes a first or distal end 60 engageable with a portion of stopper 16, a second or proximal end 62, a plunger rod body 64 extending between first end 60 and second end 62, and a flange 66 disposed adjacent second end 62.

Referring to FIGS. 1 and 2A, plunger rod 14 includes a distal end 60 that is engageable with a portion of stopper 16. In one embodiment, plunger rod 14 and stopper 16 may include engagement portions for securing plunger rod 14 to stopper 16. For example, the engagement portions may include corresponding threaded portions for securing plunger rod 14 to stopper 16. In other embodiments, the engagement portions may include a snap fit mechanism, a press-fit mechanism, a ball detent, locking tabs, spring loaded locking mechanism, latch, adhesive, or other similar mechanism. In another embodiment, plunger rod 14 and stopper 16 may be co-formed such as by co-extrusion. In this manner, plunger rod 14 is locked to stopper 16, i.e., significant relative movement between plunger rod 14 and stopper 16 is prevented and movement of plunger rod 14 can be transferred to stopper 16 to slide stopper 16 between positions within syringe barrel 12. In other embodiments, plunger rod 14 and stopper 16 may be integrally formed as a plunger assembly.

All of the components of syringe assembly 10 may be constructed of any known material, and are desirably constructed of medical-grade polymers.

A stopper 16 of the present disclosure has structural features that provide a stopper having a higher resistance to leakage, reduced syringe forces such as pump and break-loose forces, and better demolding. This is achieved and maintained after sterilization and over the lifetime of the syringe, e.g., five (5) years.

Referring to FIGS. 2A and 2B, in one embodiment, a stopper 16 of the present disclosure includes a supported stopper design. For example, stopper 16 includes a first sealing rib 56A adjacent to a stopper roof portion 70A. In one embodiment, first sealing rib 56A of stopper 16 is pinched between the internal wall surface of barrel sidewall 30 and a tip 68 of distal end 60 of plunger rod 14 as shown in FIG. 2B. In one embodiment, a stopper 16 of the present disclosure is a supported 10 ml syringe stopper design.

In other embodiments, a stopper 16 of the present disclosure includes an unsupported stopper design, e.g., the first sealing rib 56A of stopper 16 is not pinched between the syringe barrel 12 and the plunger rod 14.

Figure 3:
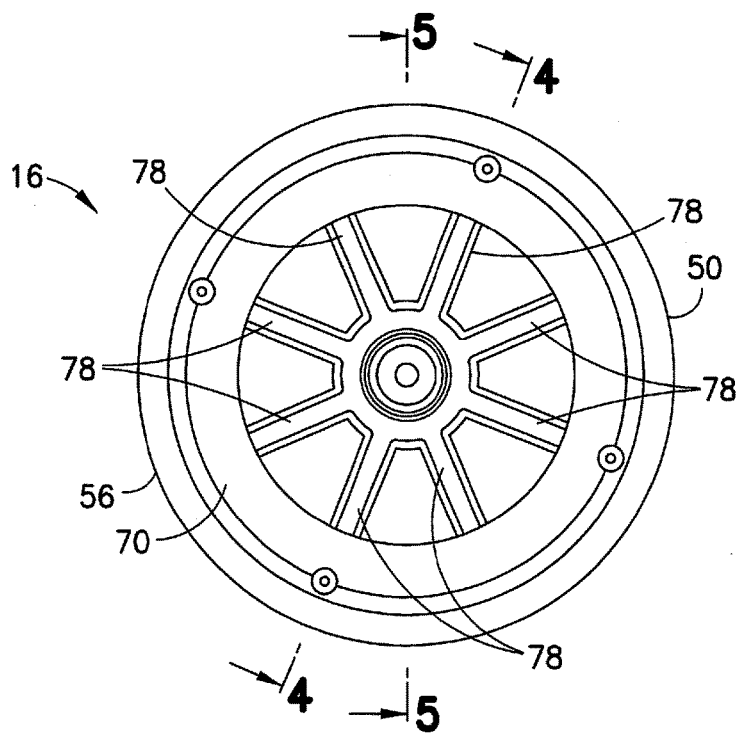
FIG. 3 is a plan view of a stopper in accordance with an embodiment of the present invention.
Figure 4:
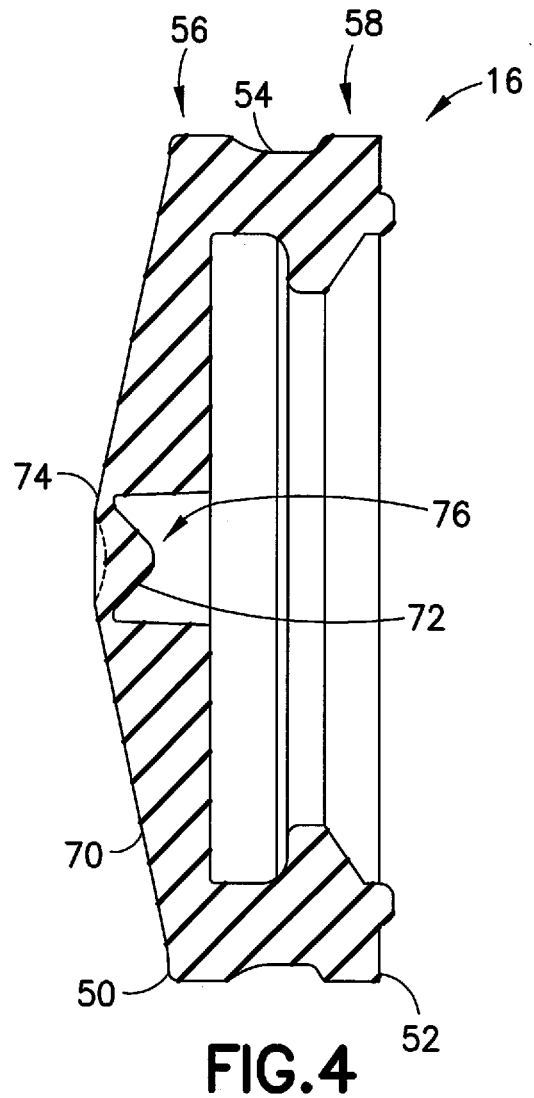
FIG. 4 is a cross-sectional view taken along line 4-4 of FIG. 3 in accordance with an embodiment of the present invention.
Figure 5:
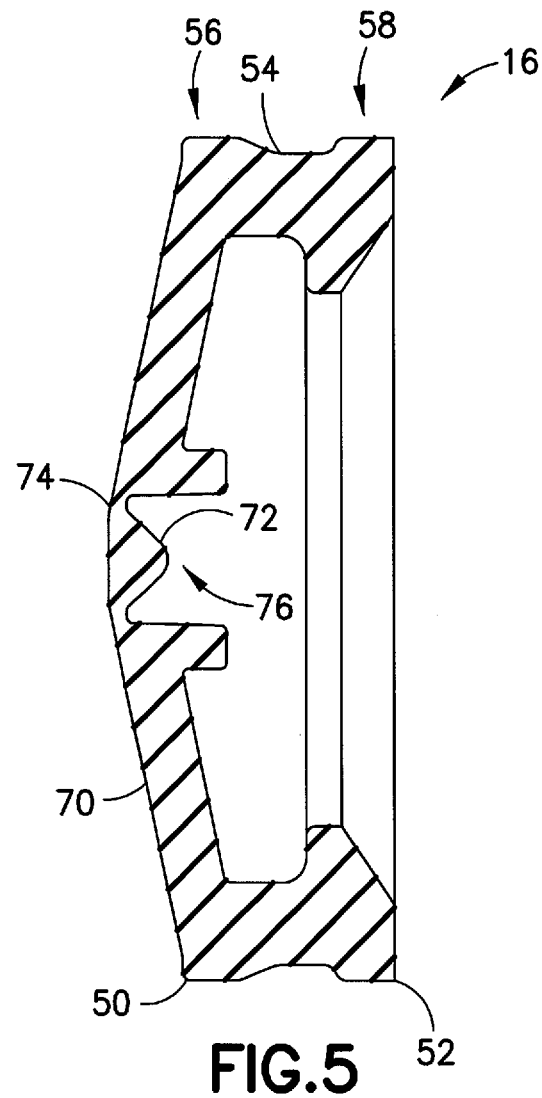
FIG. 5 is a cross-sectional view taken along line 5-5 of FIG. 3 in accordance with an embodiment of the present invention.

Referring to FIGS. 3-5, in one embodiment, stopper 16 includes an upper portion 50, a lower portion 52, and a middle portion 54 between upper portion 50 and lower portion 52. Stopper 16 includes a first sealing rib 56 located adjacent to upper portion 50 and a second sealing rib 58 located adjacent to lower portion 52. Stopper 16 also includes a roof portion 70 and a core portion 72 disposed adjacent to roof portion 70. The embodiment of stopper 16 shown in FIGS. 3-5 includes a shear element 74 and a catch can element 76 which enable molding thermoplastic elastomer stoppers in open gate systems. In one embodiment, catch can element 76 is configured to fit within the constraints of the other features of a molded part, such as enabling the shear element 74 and easy part release. The volume of catch can element 76 may be varied based on the attributes of a particular molding machine and tooling design. The catch can element 76 has a receiving volume that is at least the volume of the residual material left from a previous shot during a molding application.

Referring to FIGS. 4 and 5, first sealing rib 56A is sized and shaped to provide an active sealing rib which results in a higher resistance to leakage. For example, referring to FIG. 2B, a stopper of the present disclosure includes a first sealing rib 56A which provides a first contact area 96 with the interior surface of sidewall 30 of syringe barrel 12, and a second sealing rib 58 which provides a second contact area 98 with the interior surface of sidewall 30 of syringe barrel 12.

Referring to FIG. 15, the contact pressure of the stopper first sealing rib indicates the resistance to fluid leakage. A higher first sealing rib contact pressure leads to a higher resistance to leakage. In the active sealing rib, i.e., first sealing rib 56, design of the present disclosure, as the fluid pressure increases, the contact pressure at the stopper sealing rib increases. Thus, a stopper of the present disclosure provides a higher resistance to leakage. FIG. 15 illustrates the stopper of the present disclosure providing a higher resistance to leakage than a conventional stopper due to the above-described sealing rib design.

Referring to FIGS. 4 and 5, second sealing rib 58 includes a reduced thickness. In this manner, referring to FIG. 2B, the second contact area 98, i.e., the contact area between second sealing rib 58 and the interior surface of sidewall 30 of syringe barrel 12, is reduced. Such a reduced second contact area 98 results in a reduction of syringe forces such as pump and break-loose forces.

Referring to FIGS. 4 and 5, roof portion 70 includes an increased roof thickness which results in improved leakage performance. For example, the increased roof thickness of stopper 16 of the present disclosure results in a 20% increase in leakage pressure. The roof portion 70 of stopper 16 helps contribute to the higher contact pressure upon application of fluid pressure which leads to a higher resistance to leakage as shown in FIG. 15.

Referring to FIGS. 4 and 5, core portion 72 includes a semi-ellipsoidal shape which results in better demolding of stopper 16. The angular design of core portion 72 prevents the rupture of the stopper and increases mechanical strength of the core pin.

Figure 6:
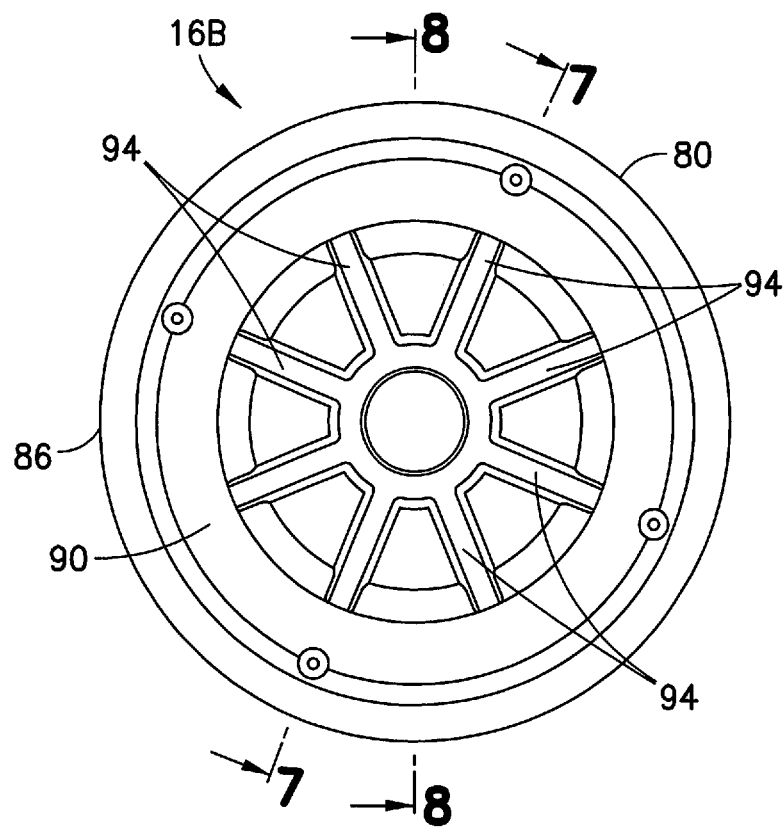
FIG. 6 is a plan view of a stopper in accordance with another embodiment of the present invention.
Figure 7:
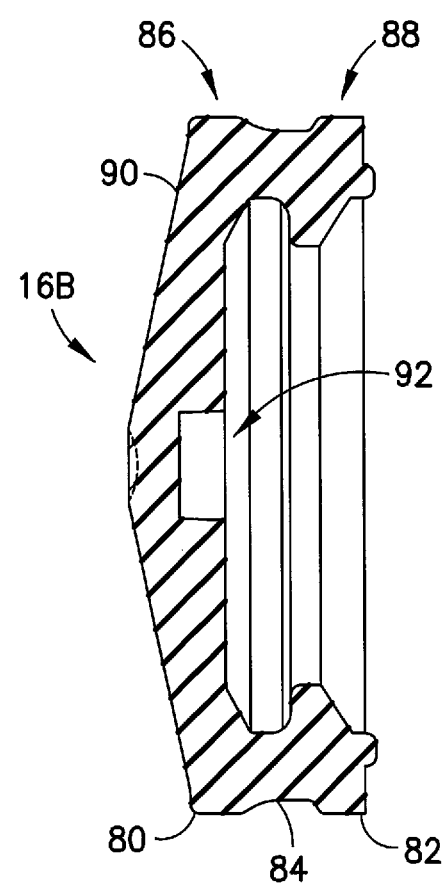
FIG. 7 is a cross-sectional view taken along line 7-7 of FIG. 6 in accordance with another embodiment of the present invention.
Figure 8:
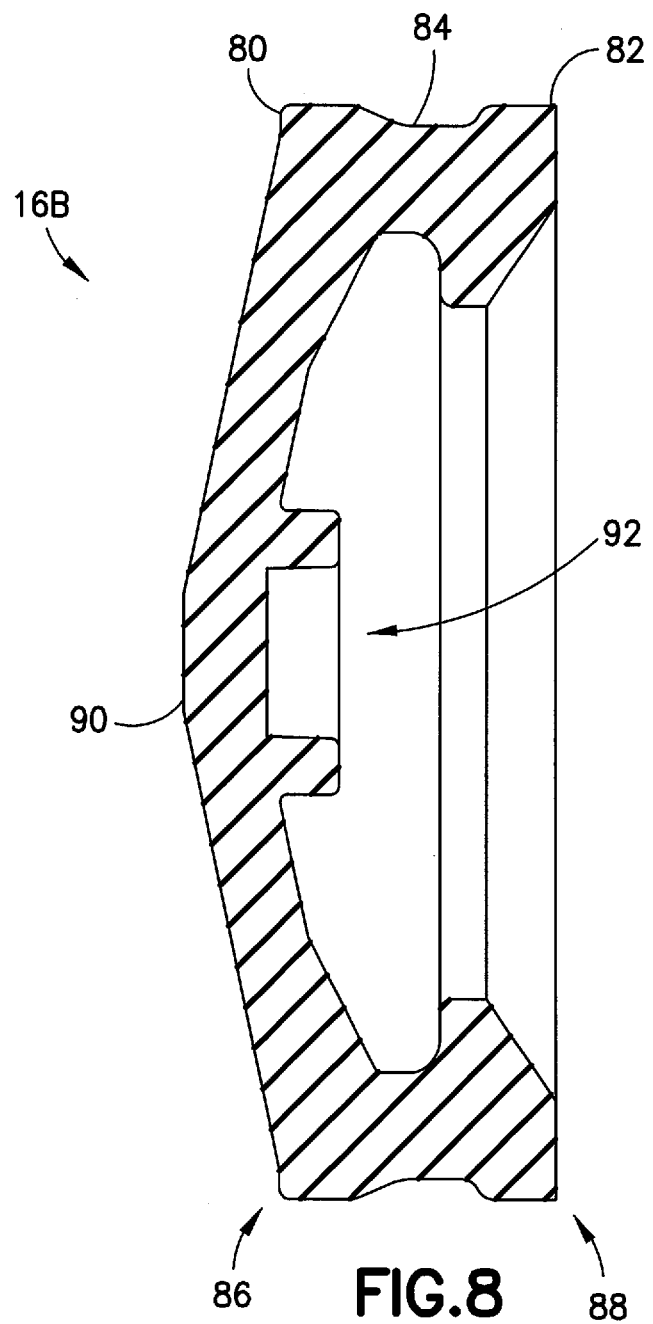
FIG. 8 is a cross-sectional view taken along line 8-8 of FIG. 6 in accordance with another embodiment of the present invention.

Referring to FIGS. 6-8, in another embodiment, a stopper 16B includes an upper portion 80, a lower portion 82, and a middle portion 84 between upper portion 80 and lower portion 82. Stopper 16B includes a first sealing rib 86 located adjacent upper portion 80 and a second sealing rib 88 located adjacent lower portion 82. Stopper 16B also includes a roof portion 90 and a core portion 92. Stopper 16B can be moldable on a valve gate system.

Referring to FIG. 8, first sealing rib 86 is sized and shaped to provide an active sealing rib which results in a higher resistance to leakage. For example, referring to FIG. 2B, a stopper of the present disclosure includes a first sealing rib 86 which provides a first contact area 96B with the interior surface of sidewall 30 of syringe barrel 12, and a second sealing rib 88 which provides a second contact area 98B with the interior surface of sidewall 30 of syringe barrel 12.

As discussed above, the higher first sealing rib contact pressure of a stopper of the present disclosure leads to a higher resistance to leakage. In the active sealing rib, i.e., first sealing rib 86, design of the present disclosure, as the fluid pressure increases, the contact pressure at the stopper sealing rib increases. Thus, a stopper of the present disclosure provides a higher resistance to leakage. FIG. 15 illustrates the stopper of the present disclosure providing a higher resistance to leakage than a conventional stopper due to the above-described sealing rib design.

Referring to FIG. 8, second sealing rib 88 includes a reduced thickness. In this manner, referring to FIG. 2B, the second contact area 98B, i.e., the contact area between second sealing rib 88 and the interior surface of sidewall 30 of syringe barrel 12, is reduced. Such a reduced second contact area 98B results in a reduction of syringe forces such as pump and breakloose forces.

Referring to FIG. 8, roof portion 90 includes an increased roof thickness which results in improved leakage performance. For example, stopper 16B of the present disclosure results in a 20% increase in leakage pressure. Referring to FIG. 8, core portion 92 includes a rectangular shape. In other embodiments, it is contemplated that core portion 92 may have other shapes. For example, core portion 92 may have an elliptical shape which helps in demolding during injection molding of stoppers.

In one embodiment, stopper 16 of an exemplary embodiment is made of a material that provides the required functional properties of a stopper without requiring an external surface of the stopper to be lubricated. For example, stopper 16 may be formed of a thermoplastic elastomer. In one embodiment, stopper 16 comprises a polyethylene based thermoplastic elastomer. In one embodiment, to reduce sticktion with syringe barrel 12 of syringe assembly 10, stopper 16 comprises a polyethylene based thermoplastic elastomer including at least 20% polyethylene with optimized material properties, e.g., hardness, compression set, stress, and strain.

In one embodiment, e.g., a TPE-2 embodiment, stopper 16 may be formed of a polyethylene blended with thermoplastic elastomer such as styrene block copolymer. In another embodiment, stopper 16 may be formed of an olefin block copolymer based with polyethylene blocks. Such embodiments with polyethylene or a similar structure such as but not limited to olefin block copolymer also reduce sticktion with syringe barrel 12 of syringe assembly 10.

Stopper 16 of the present disclosure provides a thermoplastic elastomer having reduced sticktion with a syringe barrel of a syringe assembly. Furthermore, stopper 16 of the present disclosure provides low syringe forces, such as breakloose force, breakout force, and sustaining force, and acceptable leak performance during shelf life, i.e., the duration between product manufacturing date and expiry date. Stopper 16 of the present disclosure provides such low syringe forces with low compression set that stopper 16 does not require an external surface of the stopper to be lubricated.

In an exemplary embodiment of the present disclosure, the thermoplastic elastomer composition will include 30 to 65% by weight of thermoplastic elastomer, 10 to 35% by weight of polyolefin or other high melting temperature polymer, and 20 to 35% by weight of other additives such as hydrocarbon liquid, e.g., mineral oil. In other embodiments, the other additives may include other hydrophobic liquids with a high boiling temperature to ensure that the required amount is present on and inside the stopper. In other embodiments, the olefin block copolymer with polyethylene hard phase (45 to 80%) may replace the thermoplastic elastomer and polyolefin or high melting temperature polymer.

Stopper 16 of the present disclosure does not require an external surface of the stopper to be lubricated due to the segregation of the hydrocarbon liquid such as mineral oil on the stopper surface. In this manner, the stopper surface segregated hydrocarbon liquid acts as, and replaces the need for, a lubricant and reduces the syringe operating forces. The high hydrocarbon liquid surface segregation is determined by the competition between energy and entropy of mixing. By having a stopper of the present disclosure with higher viscosity or an increase in thermoplastic elastomer molecular weight, the extent of mixing of the hydrocarbon liquid in formulation decreases and a higher extent of hydrocarbon liquid segregates to the stopper surface. In this manner, the surface segregated hydrocarbon liquid acts as, and replaces the need for, a lubricant and reduces the syringe operating forces to the level as observed with an externally lubricated stopper. Thus, a stopper of the present disclosure provides a stopper having the required functional properties of a stopper without requiring an external surface of the stopper to be lubricated, thereby eliminating the problems associated with applying a lubricant to a surface of a stopper. The problems associated with such a lubrication step include the required costs in lubricants and lubing instruments, the time and energy to operate and perform the lubrication step, and the requirement of the stopper needing to be removed from an automated assembly process to be lubricated. A stopper of the present disclosure, by eliminating the external lubrication step during assembly of a stopper, allows for complete automation of a stopper during assembly.

In one embodiment, the presence of the polyethylene at the surface of the stopper combined with the surface energy of the stopper allows for a stopper that has the required functional properties without requiring an external surface of the stopper to be lubricated, thereby eliminating the problems associated with applying a lubricant to a surface of a stopper. For example, the lower surface energy of polyethylene (~35 mJ/m$^2$) compared to polystyrene (~41 mJ/m$^2$) in a polyethylene and styrenic block copolymer blend can result in preferential segregation of polyethylene to the surface, reduced interaction between stopper and barrel material, and stiction-free performance. In a TPE-2 embodiment, stopper 16 may be formed of a polyethylene blended with styrene block copolymer. Since the hard phase of styrenic block copolymer is chemically linked to the soft phase, the polyethylene is preferentially segregated to the surface. Polypropylene is not as desired as polyolefin for a stopper application in a syringe with a polypropylene or polypropylene copolymer barrel because of the increased interaction between the polypropylene in the stopper and the barrel which may result in sticktion.

Furthermore, providing a stopper having increased thermoplastic elastomer molecular weight to achieve the viscosity requirements, also solves the high compression set problem encountered with many previous stoppers for syringe assembly application. The addition of a low viscosity hydrocarbon liquid, such as mineral oil, to the stopper of the present disclosure also improves the flow characteristics of the composition of the stopper blend at the thermoplastic elastomer processing temperature. In one embodiment, the thermal expansion coefficient of a syringe stopper can be reduced by the addition of an inorganic filler such as silica or calcium carbonate due to the low thermal expansion coefficient of such inorganic fillers and their influence on the crystalline architecture of the TPE matrix. In this manner, the addition of an inorganic filler compensates for the high coefficient of thermal expansion of a thermoplastic elastomer.

As described above, stopper 16 may be formed of a non-lubricated thermoplastic elastomer. Such a stopper 16 provides for a low compression set. For example, a non-lubricated thermoplastic elastomer stopper 16 provides a compression set equal to or lower than 35% at 25% compression for 22 hours and 70 degrees C. A stopper of the present disclosure provides the required compression set through the use of high molecular weight components.

In one embodiment of the present disclosure, a stopper for a syringe assembly includes a thermoplastic elastomer, wherein the compression set of the thermoplastic elastomer is ≤50% when measured at 25% compression for 22 hrs at 70 degrees C. In another embodiment, the compression set of the thermoplastic elastomer is approximately ≤35% when measured at 25% compression for 22 hrs at 70 degrees C. In another embodiment, the compression set of the thermoplastic elastomer is approximately 10%-35% when measured at 25% compression for 22 hrs at 70 degrees C.

A low compression set is desired for a syringe stopper application as the interference of a stopper with a barrel dictates both syringe use forces and leak performance. In the case of a high compression set, the syringe leak and force performance would be fine after assembly but the leak performance would suffer during the syringe shelf life as shown in FIG. 20. FIG. 20 illustrates that a TPE stopper material with a compression set level above 50% (ASTM D395-03, Method B, 22 hrs at 70° C.) has poor leakage performance during syringe shelf life.

Furthermore, stopper 16 of the present disclosure provides a better hand feel of syringes with a plurality of different fluids. For example, the hand control of filling a syringe with a fluid without a needle attached is improved and the use of stopper 16 of the present disclosure with a syringe assembly provides good control at the droplet level, e.g., placing a droplet of blood on a slide for evaluation. By improving the hand control of a syringe assembly, a clinician is able to smoothly deliver a fluid to a patient thereby reducing any patient discomfort. Furthermore, by improving the hand control of a syringe assembly, any squirt of a fluid leading to contamination is eliminated. A stopper of the present disclosure provides the improved hand control properties through the use of high molecular weight components. Additionally, a stopper of the present disclosure utilizes the higher viscosity of TPE to provide a stopper that provides the above-described functional performance factors for a syringe assembly while eliminating the external lubricant on a stopper. For example, stoppers formed of a lower viscosity than the TPE-2 embodiment of the present disclosure may have bad control with spurting with isopropanol and blood. Thus, the higher viscosity of the TPE-2 embodiment of the present disclosure is an important factor for the good hand control factors.

Figure 14A:
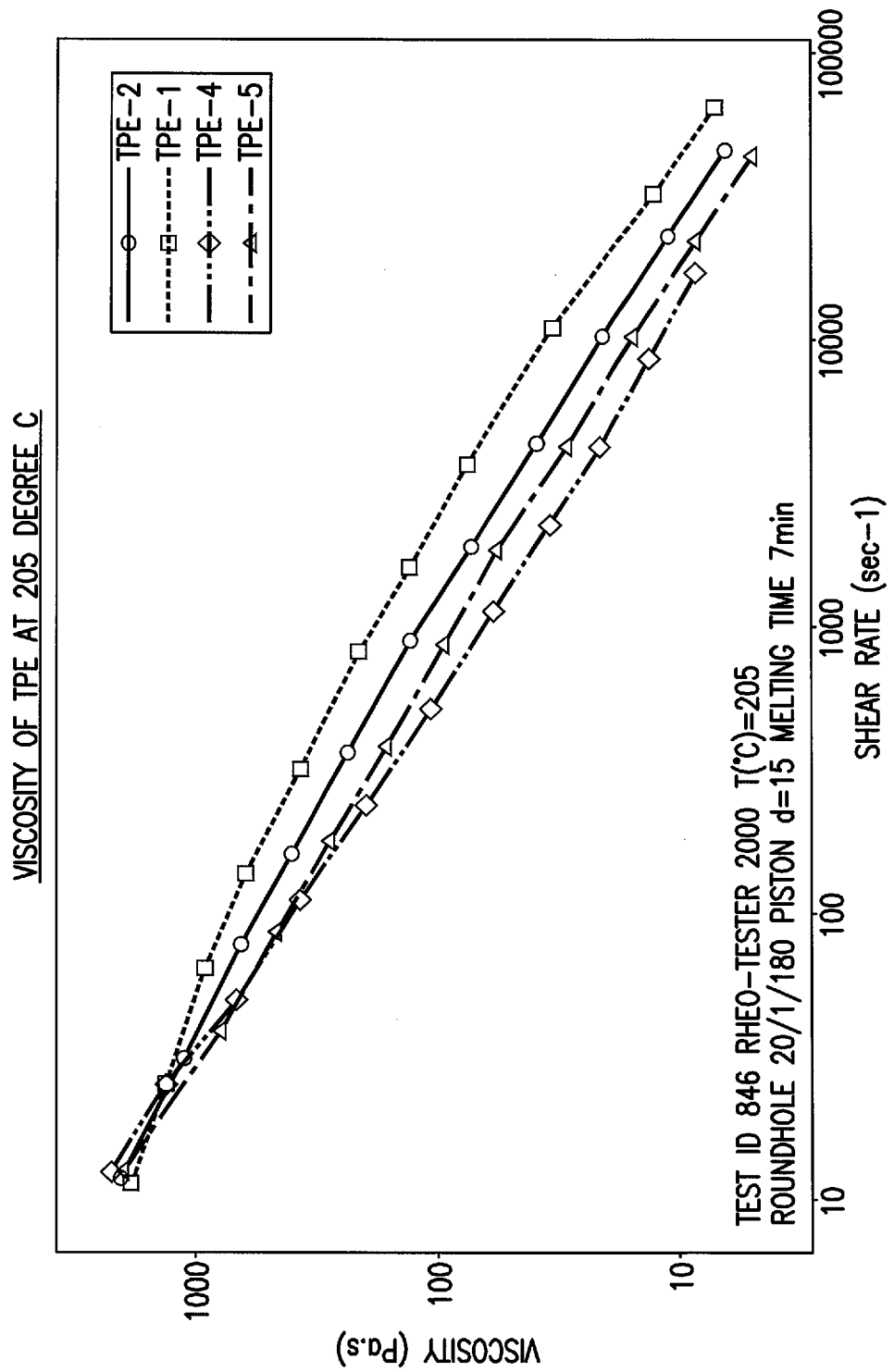
FIG. 14A is a graph of the viscosity and shear rate of various stoppers in accordance with an embodiment of the present invention.

Referring to FIG. 14B, a table is provided showing the improved hand control properties of a stopper of the present disclosure formed of an Olefin block copolymer, e.g., a TPE-1 embodiment, and of a stopper of the present disclosure formed of a polyethylene blended with styrenic block copolymer, e.g., a TPE-2 embodiment. The TPE-4 embodiment, which is a polypropylene blended with styrene block copolymer formulation with lower viscosity than TPE-1 and TPE-2 embodiments, exhibits bad liquid control with spurting (FIG. 14A). The TPE-5 embodiment, which is also based on polyethylene blended with styrene block copolymer, similar to TPE-2 but of lower viscosity (such as shown in FIG. 14A), also exhibit poor liquid control with spurting. A minimum viscosity of the TPE formulation, as documented for the embodiments in this disclosure, is required for good hand control of stopper formulations when used in syringe applications.

With reference to FIG. 14B, a stopper of the present disclosure is formed of a TPE with a high viscosity that provides additional advantages such as no external lubricant on the stopper and improved hand control over conventional stoppers. A stopper of the present disclosure provides for improved and/or preferred maintenance of the hand control of the syringe with fluids, and/or limited excipient interactions. A stopper of the present disclosure formed of a high viscosity TPE helps in achieving better hand control with different fluids. A stopper of the present disclosure formed of a high viscosity TPE provides for improved and/or preferred excipient interaction or hand control of syringe with fluids. Different hand control of fluids can be observed such as good control at droplet level (best control), good control but stream of fluid instead of droplet comes out on the start of plunger motion, good control with droplet level at start but spurting during the middle of fluid injection, starts with spurt but control improves later, and starts with spurt and no control during fluid injection or bad control with spurting (worst control).

Slip additives are commonly added in the TPE formulation to decrease the coefficient of friction. An unexpected effect was observed on syringe hand control by the presence of a slip additive in TPE stopper formulation (along with the impact of formulation viscosity on this performance as shown in FIG. 14A). By adding a slip additive, such as but not limited to Erucamide, Oleamide, or Behenamide at concentrations less than 1%, the hand control significantly improves above a critical concentration of slip additive as shown in FIG. 26. The presence of a slip additive in TPE stopper formulation also impacts syringe forces, as expected by the decrease in friction coefficient as shown in FIG. 22.

Referring to FIG. 21, a stopper of the present disclosure is formed of a high viscosity TPE. Viscosity below a critical level leads to poor excipient hand control with spurting of fluid during injection. In one embodiment of the present disclosure, the viscosity of the thermoplastic elastomer is ≥70.0 Pa·s at 1,000 s$^{-1}$ shear rate, ≥12.0 Pa·s at 10,000 s$^{-1}$ shear rate, and ≥3.0 Pa·s at 50,000 s$^{-1}$ shear rate when measured using a capillary rheometer at 205 degrees C. (Die: Roundhole 20 mm length/1 mm diameter/180 degree inlet, Piston: d=15 mm, and melting time=7 min). In one embodiment, the viscosity of the thermoplastic elastomer is from 70.0 Pa·s to 320.0 Pa·s at 1,000 s$^{-1}$ shear rate. In another embodiment, the viscosity of the thermoplastic elastomer is from 100.0 Pa·s to 170.0 Pa·s at 1,000 s$^{-1}$ shear rate. In another embodiment, the viscosity of the thermoplastic elastomer is from 12.0 Pa·s to 46.0 Pa·s at 10,000 s$^{-1}$ shear rate. In another embodiment, the viscosity of the thermoplastic elastomer is from 16.0 Pa·s to 27.0 Pa·s at 10,000 s$^{-1}$ shear rate. In another embodiment, the viscosity of the thermoplastic elastomer is from 3.0 Pa·s to 12.0 Pa·s at 50,000 s$^{-1}$ shear rate. In one embodiment, the viscosity of the thermoplastic elastomer is from 4.5 Pa·s to 7.5 Pa·s at 50,000 s$^{-1}$ shear rate.

A stress-strain curve is a material property that characterizes the behavior of a particular material. The linear portion of the stress-strain curve is governed by a relationship known as Hooke's Law. For a stopper, this stress-strain relationship is converted into an appropriate material model that acts as one of the inputs to FEA during the design process.

In one embodiment, the stress at desired strain values is also optimized for the thermoplastic elastomer stopper of the present disclosure so as to obtain good leak and force performance with an assembled syringe. Referring to FIG. 11, a table with the desired stress values is provided.

Referring to FIGS. 11-14B, in one embodiment, e.g., a TPE-1 embodiment, stopper 16 may be formed of an olefin block copolymer. In another embodiment, e.g., a TPE-2, TPE-3 or TPE-5 embodiment, stopper 16 may be formed of a polyethylene blended with styrenic block copolymer. In another embodiment, e.g., a TPE-4 embodiment, stopper 16 may be formed of a polypropylene blended with styrenic block copolymer. Conventional based stoppers may be formed of a styrenic based or polyisoprene based material.

The present disclosure provides for a thermoplastic elastomer stopper that meets the desired material properties and design of a stopper for a syringe assembly. Referring to FIGS. 12 and 13, tables are provided demonstrating the importance of the design and the desired physical properties for the material of a stopper of the present disclosure. It is noted herein that test method "IT" shown in FIG. 12 adheres to ISO standard 7886-1:1993. In one embodiment, the material properties may include compression set, hardness, stress at given strain levels, and viscosity at given shear rates. In one embodiment, the compression set of a thermoplastic elastomer stopper of the present disclosure may be ≤50% when measured at 25% compression for 22 hrs at 70 degrees C. (ASTM D395-03, Method B). In one embodiment, the hardness of a thermoplastic elastomer stopper of the present disclosure should be in the range of 40-70 Shore A (ASTM D2240-05). The stress at desired strain values should also be optimized for the thermoplastic elastomer stopper of the present disclosure so as to obtain good leak and force performance with the assembled syringe. In one embodiment, the viscosity of a thermoplastic elastomer stopper of the present disclosure may be >70.0 Pa·s at 1,000 s$^{-1}$ shear rate, >12.0 Pa·s at 10,000 s$^{-1}$ shear rate, and >3.0 Pa·s at 50,000 s$^{-1}$ shear rate. In one embodiment, a thermoplastic elastomer stopper of the present disclosure provides for stiction-free performance with a polypropylene or polypropylene copolymer based barrel. For example, a stopper of the present disclosure includes a 30-65% thermoplastic elastomer such as but not limited to 30-65% styrene-ethylene-butylene-styrene (SEBS) copolymer blended with 10-35% polyolefin or higher melting temperature polymer such as but not limited to 10-35% medium to high density polyethylene (medium to high density with melting temperature of from 120 degrees C. to 130 degrees C.) but excluding polypropylene, 20-35% commonly available mineral oil along with commonly available radiation stabilizer, antioxidant, and/or processing aids. The molecular weight of the SEBS and polyethylene are selected so as to obtain the desired material properties as described above.

The important characteristics of the materials used to make stopper 16 is that stopper 16 is made of a material that along with design for low forces provides the required functional properties of a stopper without requiring an external surface of the stopper to be lubricated. Stopper 16 of an exemplary embodiment may have the following material properties. In one embodiment, it is contemplated that stopper 16 has a stopper material hardness of approximately 45 Shore A Hardness to approximately 65 Shore A Hardness. In some embodiments, it is contemplated that stopper 16 has a stopper material hardness of approximately 53 Shore A Hardness to approximately 63 Shore A Hardness.

The present disclosure provides for a thermoplastic elastomer stopper that meets the desired material properties of a stopper for a syringe assembly. These material properties include hardness and compression set. These properties along with findings that no more than a critical defined concentration of barrel material in the stopper formulation and high viscosity resin used in the stopper formulation results in stoppers of improved performance, e.g., better syringe control during hand injection and pump use. The desired range for hardness of a stopper of the present disclosure is reflected by the desired stress values at given strain levels as shown in FIG. 11. A syringe stopper has two competing requirements, good leakage performance and low operating forces, and they are met by a stopper material of a required hardness. A stopper material of a low hardness would have poor leak performance and a stopper material of a high hardness would have a high (undesired) force performance resulting in a leakage of the fluid in the barrel past the stopper ribs.

A stopper of the present disclosure also provides a sticktion-free syringe stopper manufactured from the composition of the present disclosure. An autoclavable syringe can be obtained with the use of high melting temperature polymer in formulation.

Conventional autoclavable stoppers generally are formed of thermoset rubbers coated with a lubricant. However, manufacturing of such conventional autoclavable stoppers requires multiple processing steps and generates increased excess waste.

Conventionally, a thermoplastic elastomer stopper based on polypropylene blends can also be used in autoclavable syringes. The autoclavablitiy of such syringes is obtained by the addition of a lot of inorganic fillers into a stopper formulation to provide structural integrity at autoclaving temperatures. The use of inorganic fillers damages the surface of the mold resulting in reduced efficiency and high running costs. Also, the presence of inorganic fillers in the composition results in issues associated with extractables and leachables during use and storage of syringes. Therefore, there is a need for a thermoplastic elastomeric composition for the manufacturing of syringe stoppers which can be autoclaved without the need for inorganic fillers.

As discussed above, a stopper of the present disclosure is made of a material that provides the required functional properties of the stopper without requiring an external surface of the stopper to be lubricated. For example, a stopper of the present disclosure may be formed of a thermoplastic elastomer. In this manner, a stopper of the present disclosure also allows for an autoclavable stopper for a syringe assembly.

In one embodiment, the thermoplastic elastomer composition of a stopper of the present disclosure is based on high melting temperature polymers. For example, a melting temperature ≥170 degrees C. is required for autoclavable syringes.

As previously discussed, in one embodiment, a stopper of the present disclosure may be formed of a thermoplastic elastomer composition including a blend of injection moldable elastomers including block copolymers and a high transition temperature polymer. In some embodiments, the elastomer may include a styrene block copolymer, an olefin block copolymer, polyisoprene, and butyl rubber blended with the high transition temperature polymers which may include ethylene-tetrafluoro-ethylene (ETFE) and fluorinated ethylene propylene (FEP) polymers.

In one embodiment, the composition of a stopper of the present disclosure may include 30 to 65% by weight of elastomers such as but not limited to styrene block copolymer and olefin block copolymer, 10 to 35% by weight of high transition temperature polymers such as but not limited to ethylene-tetrafluoro-ethylene, and 20-35% by weight of other additives such as mineral oil to meet the desired processing requirements and material properties such as hardness, tensile, viscosity, and compression set properties for a stopper for a syringe assembly application. In other embodiments, the composition of a stopper of the present disclosure contains a radiation stabilizer, an antioxidant, and/or a processing aid.

A stopper of the present disclosure overcomes the deficiencies of conventional stoppers by providing an injection moldable thermoplastic syringe stopper wherein the sticktion free performance is generated by the migration to the surface of hydrocarbon liquids such as mineral oil incorporated in the composition of the stopper. The high temperature stable polymer at the level of at least 10 to 35% by weight in the composition provides structural integrity during autoclaving processes and any other exposure to high temperature conditions. For example, the high transition temperature polymers may include ethylene-tetrafluoro-ethylene (ETFE) and fluorinated ethylene propylene (FEP) polymers. As discussed above, the thermoplastic elastomer composition of a stopper of the present disclosure is based on high melting temperature polymers. For example, a melting temperature ≥170 degrees C. is required for autoclavable syringes. In this manner, a stopper of the present disclosure results in a lubricant free, sticktionless, autoclavable, and injection moldable stopper while eliminating the step of an external lubrication on a stopper.

A stopper of the present disclosure also provides additional advantages relating to manufacturing and/or molding. For example, in one embodiment, a stopper of the present disclosure includes a shear-feature, i.e., a thin-wall section, at the mold gating point within a mold cavity. The shear-feature of a stopper of the present disclosure adds shear heat at the mold gate point. In this manner, a stopper of the present disclosure eliminates cold material from entering the mold cavity, eliminates flow lines and/or weld lines common to stopper molding, eliminates sink marks, improves the control of gate quality, improves the mold cycle time, and eliminates surface and/or visual imperfections.

As described above, the embodiment of stopper 16 shown in FIGS. 3-5 includes shear element 74 and catch can element 76 which enable molding thermoplastic elastomer stoppers in open gate systems. Open gate systems can also be referred to as hot tip systems. In one embodiment, shear element 74 has a thickness that is less than 52% and greater than 36% of the thickness of roof portion 70 of stopper 16.

In one embodiment, shear element 74 has a thickness that is approximately 44% of the thickness of roof portion 70 of stopper 16. In one embodiment, shear element 74 is approximately 50% of the general wall thickness at the gate location. In one embodiment, shear element 74 has a thickness of 0.012 inches. In one embodiment, shear element 74 has a thickness of 0.018 inches. In one embodiment, shear element 74 has a thickness of 0.023 inches.

In a conventional open gate hot runner system, the gate cannot close off causing residual heat and pressure which results in a small amount of unmelted and/or slightly melted residual resin left from the previous shot. This material then gets pushed in and incorporated into the stopper, or other molded part, during the next shot. Furthermore, this residual material can go anywhere within the molded part. If the residual material lands on the surface of the stopper it will compromise the aesthetic quality of the part and depending on the location could cause functional performance issues. For example, if the residual unmelt lands on the surface of the stopper rib it will impede the stopper from sealing to the barrel wall and result in leakage and a product failure. This residual material compromises the quality and performance of the molded part, increasing scrap rate and thus resulting increased cost.

Referring to FIGS. 4 and 5, catch can element 76 is designed to enable easy part release. Catch can element 76 is designed to fit within the constraints of other features of the molded part, to enable the shear feature and optimize easy part release. Catch can element 76 is also designed to fit within the constraints of the other features of the molded part, such as enabling shear element 74. Catch can element 76 includes a receiving volume which is dependent on attributes of the molding machine and tooling design. In one embodiment, catch can element 76 has a volume that is at least the volume of the residual material left from the previous shot. In one embodiment, catch can element 76 needs to be of a sufficient volume that is dictated by the hot runner drop and located opposite the gate.

Figure 27:
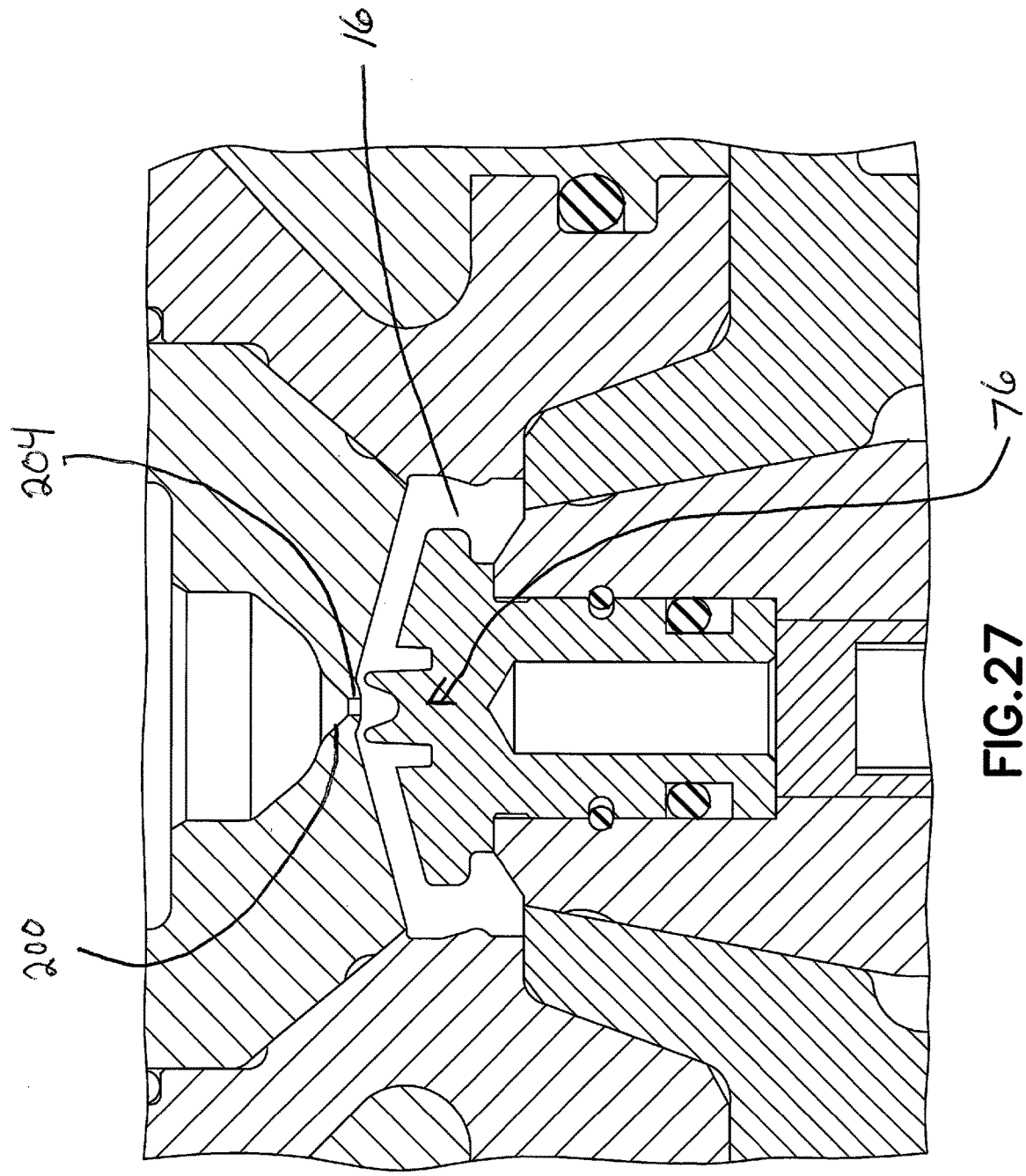
FIG. 27 is a cross-sectional view of a thermoplastic elastomer stopper and a hot-tip portion of a hot runner system in accordance with an embodiment of the present invention.

Referring to FIG. 27, the catch can element 76 and a hot-tip portion 200 of a hot runner system is illustrated. In one embodiment, a gate portion 204 adjacent the stopper 16 is capable of slowly moving into the catch can element 76. In this manner, the residual material can be trapped within the catch can element 76 so that it will not flow into the molding area of the stopper 16 causing flow lines and/or knit lines in portions of the stopper 16.

Referring to FIG. 28, a cold slug 210 of TPE sets up at the end of the hot tip 212 at the end of the molding cycle that is then injected into the cavity the following cycle. This cold material does not re-melt back into the flow path of the new material and can become lodged in a sealing rib of the stopper 16, causing a leakage path. The catch can element 76 needs to be of a sufficient size to capture the cold slug 210 and the shear element 74 gap needs to be small enough to keep the cold slug 210 from passing through with the good TPE, similar to a strainer. The geometry of the catch can element 76 and the shear element 74 are governed by the size of the gate slug that is produced by the hot-tip hot runner system, not the size of the stopper being molded.

Referring to FIG. 5, core portion 72 includes a shape which results in better demolding of stopper 16. The angular position of core portion 72 prevents rupture of the stopper and improves mechanical strength of the core pin.

Referring to FIG. 2B, core portion 72 includes a semi-ellipsoidal shape 79 that has a radius that helps in distributing the plastic in cavity. The semi-ellipsoidal shape 79 also adds strength to the stopper 16 and improves the ejection of the center of the stopper 16.

Referring to FIGS. 3 and 6, a stopper of the present disclosure also includes umbrella arm elements 78, 94. Umbrella arm elements 78, 94 enable a fully supported stopper roof with the plunger rod without requiring full contact across the whole under stopper surface area. Umbrella arm elements 78, 94 decrease cycle time and reduce the amount of resin used per shot. In this manner, umbrella arm elements 78, 94 provide a cost savings in production output and in raw material. Also, umbrella arm elements 78, 94 provide an environmentally green advantage by providing a system that requires less raw material.

As previously discussed, the problems of excessive breakout and breakloose forces are related to friction. Friction is generally defined as the resisting force that arises when a surface of one substance slides, or tends to slide, over an adjoining surface of itself or another substance. Between surfaces of solids in contact, there may be two kinds of friction: (1) the resistance opposing the force required to start to move one surface over another, conventionally known as static friction, and (2) the resistance opposing the force required to move one surface over another at a variable, fixed, or predetermined speed, conventionally known as kinetic friction.

The force required to overcome static friction and induce breakout is referred to as the "breakout force", and the force required to maintain steady slide of one surface over another after breakout or breakloose is referred to as the "sustaining force". Two main factors contribute to static friction and thus to the breakout or breakloose force. The term "stick" as used herein denotes the tendency of two surfaces in stationary contact to develop a degree of adherence to each other. The term "inertia" is conventionally defined as the indisposition to motion which must be overcome to set a mass in motion. In the context of the present invention, inertia is understood to denote that component of the breakout force which does not involve adherence.

Breakout or breakloose forces, in particular the degree of stick, vary according to the composition of the surfaces. In general, materials having elasticity show greater stick than non-elastic materials, particularly when the surfaces are of similar composition. The length of time that surfaces have been in stationary contact with each other also influences breakout and/or breakloose forces. In the syringe art, the term "parking" denotes storage time, shelf time, or the interval between filling and discharge. Parking generally increases breakout or breakloose force, particularly if the syringe has been refrigerated during parking.

As discussed, conventional stoppers require the application of a lubricant to a surface of a stopper. The present disclosure provides a stopper that is made of a material that provides the required functional properties of a stopper without requiring an external surface of the stopper to be lubricated.

Figure 9:
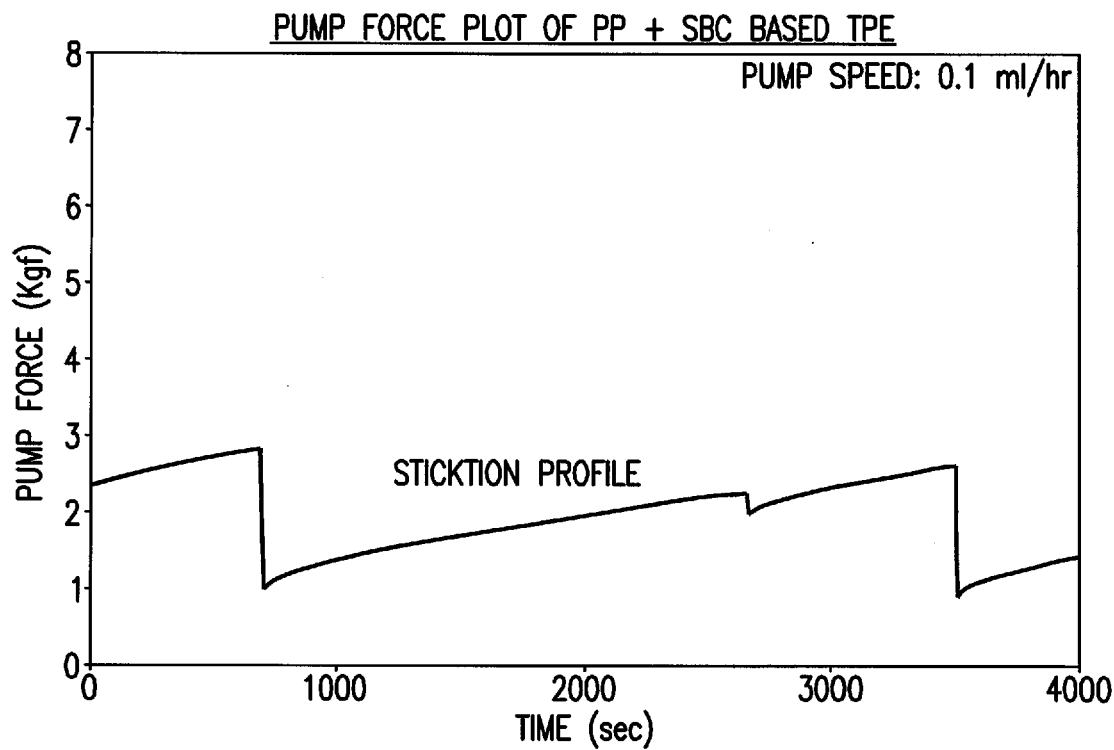
FIG. 9 is a graph of a conventional stopper exhibiting sticktion in accordance with an embodiment of the present invention.

Referring to FIG. 9, a thermoplastic elastomer stopper based on a styrene block copolymer blended with polypropylene in combination with a polypropylene barrel exhibits sticktion, i.e., in a stationary position, the stopper develops a degree of adherence to the interior surface of a syringe barrel and requires a breakloose force to overcome the friction between the stopper and the interior surface of the polypropylene syringe barrel. The sticktion between the stopper and the syringe barrel makes it difficult to provide smooth incremental line-to-line advancement of the stopper within the syringe barrel.

Figure 10:
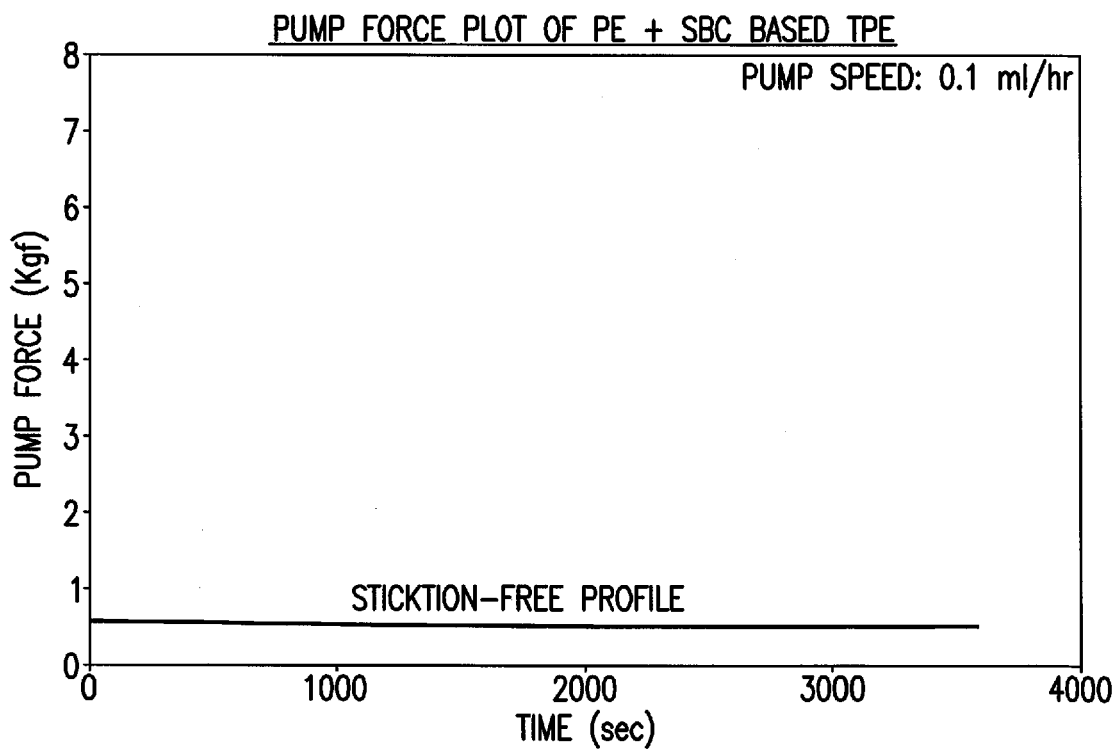
FIG. 10 is a graph of a stopper that does not exhibit sticktion in accordance with an embodiment of the present invention.

Referring to FIG. 10, a stopper of the present disclosure based on a styrene block copolymer blended with polyethylene, which does not require an external surface of the stopper to be lubricated due to the segregation of the hydrocarbon liquid such as mineral oil on the stopper surface, does not exhibit sticktion and provides the smooth incremental line-to-line advancement of the stopper within the syringe barrel. This allows for a fluid to be dispensed from a syringe assembly in accurately controlled quantities. In other embodiments, a stopper of the present disclosure formed of an olefin block copolymer exhibits the sticktion-free performance, similar to as shown in FIG. 10.

In one embodiment, syringe barrel 12 is formed of a first material and stopper 16 is formed of a second material different than the first material, wherein the second material does not contain more than 4% of the first material and more preferably the second material does not contain more than 1.5% of the first material and still more preferably the second material does not contain more than 1% of the first material. For example, stopper 16 may be formed of a polyethylene based thermoplastic elastomer and syringe barrel 12 may be formed of a polypropylene. In other embodiments, stopper 16 may be formed of a polyisoprene or SBR material and syringe barrel 12 may be formed of a glass, cycloaliphatic polyolefins, polyesters, or polycarbonate material. In this manner, the degree of adherence that the stopper develops to the interior surface of a syringe barrel is reduced, e.g., the chemical interaction between the stopper and the syringe barrel is mitigated, and the stopper and the syringe barrel do not exhibit sticktion and the syringe assembly provides smooth incremental line-to-line advancement of the stopper within the syringe barrel. This allows for a fluid to be dispensed from a syringe assembly in accurately controlled quantities.

The tests, research, and experimentation of the present disclosure were conducted for stopper stick-slip motion at a low speed (0.1 ml/hr with 10 ml syringe configuration) with polypropylene (PP) barrel and PP content in a TPE stopper as shown in FIG. 17. Smooth stopper motion is desired for continuous drug delivery at low rates. As can be observed in FIG. 17, at PP concentrations of 1% and lower, there is no stick-slip stopper motion. In contrast, the stick-slip motion occurrences increases above this critical PP concentration and is exhibited by all syringes at PP concentrations of 5.7% and higher. These results would translate similarly to a barrel of an alternate resin composition and that same resin being incorporated into the stopper formulation.

The composition of the thermoplastic stopper resin should not have the same material as in the barrel so as to avoid sticktion. For example with a polypropylene or polypropylene copolymer based barrel, the stopper formulation should not be polypropylene based. A thermoplastic elastomer with formulation based on lower surface tension hard phase also helps in reducing sticktion. For example, styrenic block copolymer (polystyrene surface tension ~41 mN/m) mixed with polyethylene (surface tension ~35 mJ/m$^2$) or ETFE (~23 mN/m$^2$) results in preferential surface segregation of hard phase and reduced interaction with the barrel.

In syringe assemblies including a stopper and a syringe barrel formed of the same material, the chemical interaction between the stopper and the syringe barrel is increased and it results in sticktion between the stopper and the syringe barrel. For example, during the stationary position, the stopper develops a degree of adherence to the inner surface of the barrel and requires a breakloose force (typically higher than the sustaining force) which is the force required to overcome the static friction between the surfaces of the stopper and the syringe barrel. In extreme cases, adhesion between the barrel and stopper can develop at slower motions making it difficult to provide smooth incremental line-to-line advancement of the stopper within the syringe barrel. In the case of pump application syringes with such a stopper, the drug delivery would not be smooth and thus is not desirable. For polypropylene (PP) based barrels, the stopper should not have above a critical level of PP in its formulation, as shown in FIG. 17, for smooth or no stick-slip motion during pump usage (pump speed of 0.1 ml/hr using 10 ml syringe). The PP content in these formulations was calculated using energy of melting from DSC corresponding to PP, energy of melting of 100% crystalline PP as 293 J/g, and assuming 50% PP crystallinity in stopper material. The DSC peak associated with PP melting was not identifiable in TPE-1, TPE-2 (all slip agent levels), TPE-3, TPE-5, and TPE-6 indicating that the PP content in these TPE is <1%. FIG. 17 indicates that formulations TPE-4, TPE-10, TPE-11, TPE-12, TPE-13, TPE-14, and TPE-15 have PP content >1% and fails the stick-slip performance requirement. An example of a syringe pump force profile for TPE-2-S0.6 and TPE-4 (silicone lubricant lubed) are shown in FIGS. 9 and 10. Even though TPE-6 has a PP content <1%, TPE-6 fails to meet the no sticktion performance. This is due to the minimum amount of polyethylene required in a styrenic block copolymer stopper system.

Based on the research and experimentation of the present disclosure, if the syringe barrel 12 is formed of a first material and the stopper 16 is formed of a second material different than the first material, wherein the second material does not contain more than 4% of the first material and more preferably the second material does not contain more than 1.5% of the first material and still more preferably the second material does not contain more than 1% of the first material, then the stick-slip motion of the stopper against the plunger rod is avoided. For example, as described above, stopper 16 may be formed of a polyethylene based thermoplastic elastomer and syringe barrel 12 may be formed of a polypropylene. In other embodiments, stopper 16 may be formed of a polyisoprene or SBR material and syringe barrel 12 may be formed of a glass, cycloaliphatic polyolefins, polyesters, or polycarbonate material. In this manner, as described above, the degree of adherence that the stopper develops to the interior surface of a syringe barrel is reduced, e.g., the chemical interaction between the stopper and the syringe barrel is mitigated, and the stopper and the syringe barrel do not exhibit sticktion and the syringe assembly provides smooth incremental line-to-line advancement of the stopper within the syringe barrel. This allows for a fluid to be dispensed from a syringe assembly in accurately controlled quantities.

Breakout or breakloose forces, in particular the degree of stick, vary according to the composition of the surfaces. In general, materials having elasticity show greater stick than non-elastic materials, particularly when the surfaces are of similar composition. The length of time that surfaces have been in stationary contact with each other also influences breakout and/or breakloose forces. In the syringe art, the term "parking" denotes storage time, shelf time, or the interval between filling and discharge. Parking generally increases breakout or breakloose force, particularly if the syringe has been refrigerated during parking.

As is known in the art, conventional stoppers require the application of a lubricant to a surface of a stopper. The present disclosure provides a stopper that is made of a material that provides the required functional properties of a stopper without requiring an external surface of the stopper to be lubricated. A stopper of the present disclosure includes a stopper material having a high enough viscosity which is made possible by a high molecular weight of the elastomer and/or a hard phase of the formulation. The mineral oil incorporated in the formulation segregates to the stopper surface due to a low entropy of mixing and satisfies the role played by externally applied silicone lubricant on a conventional syringe stopper surface.

FIG. 13 documents the hand forces for lubed and unlubed TPE stoppers in a 10 ml embodiment after gamma sterilization. The syringe hand forces are similar for syringes with lubed and unlubed stoppers.

Figure 18:
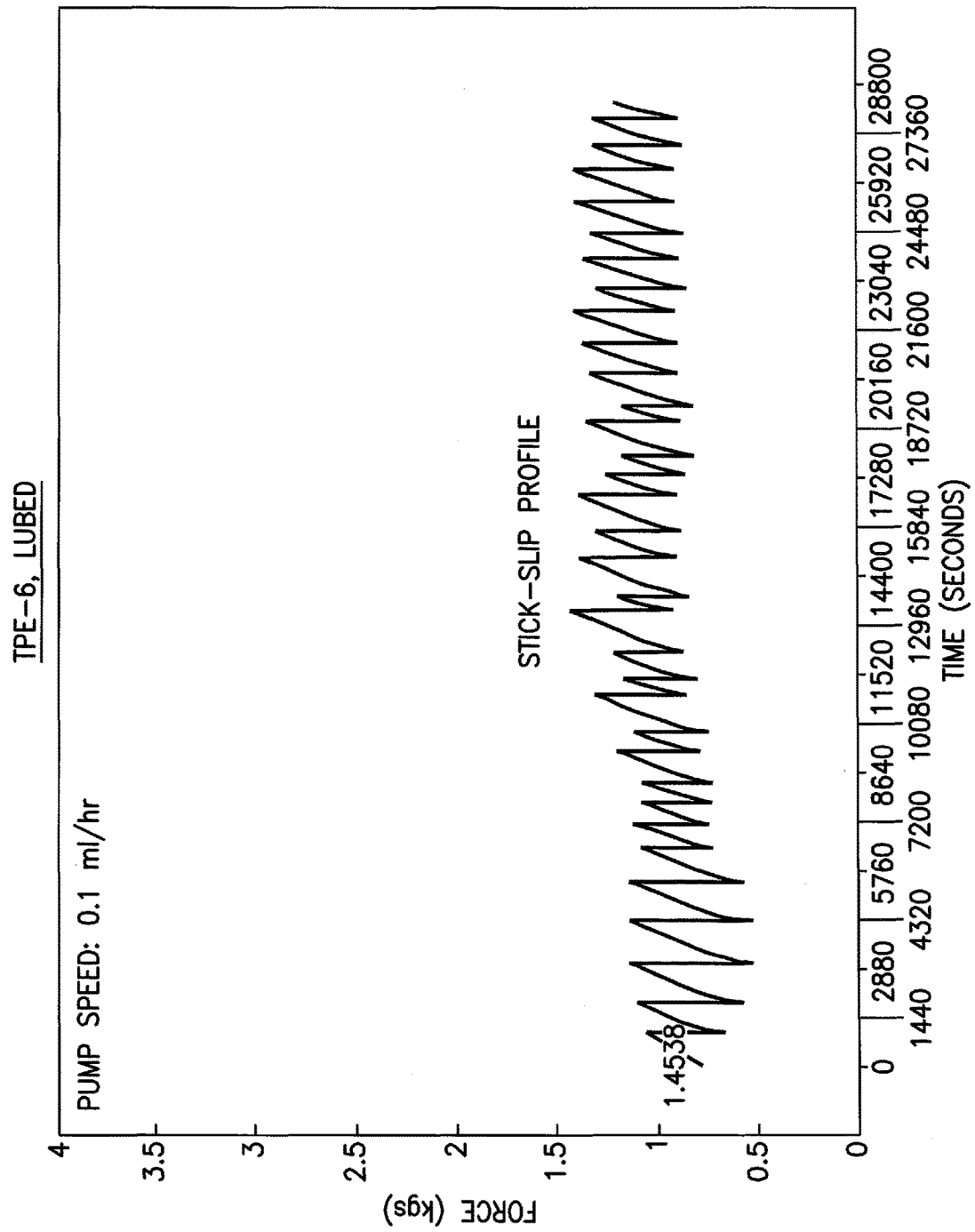
FIG. 18 is a graph of a pump force profile of a thermoplastic elastomer stopper in accordance with an embodiment of the present invention.
Figure 19:
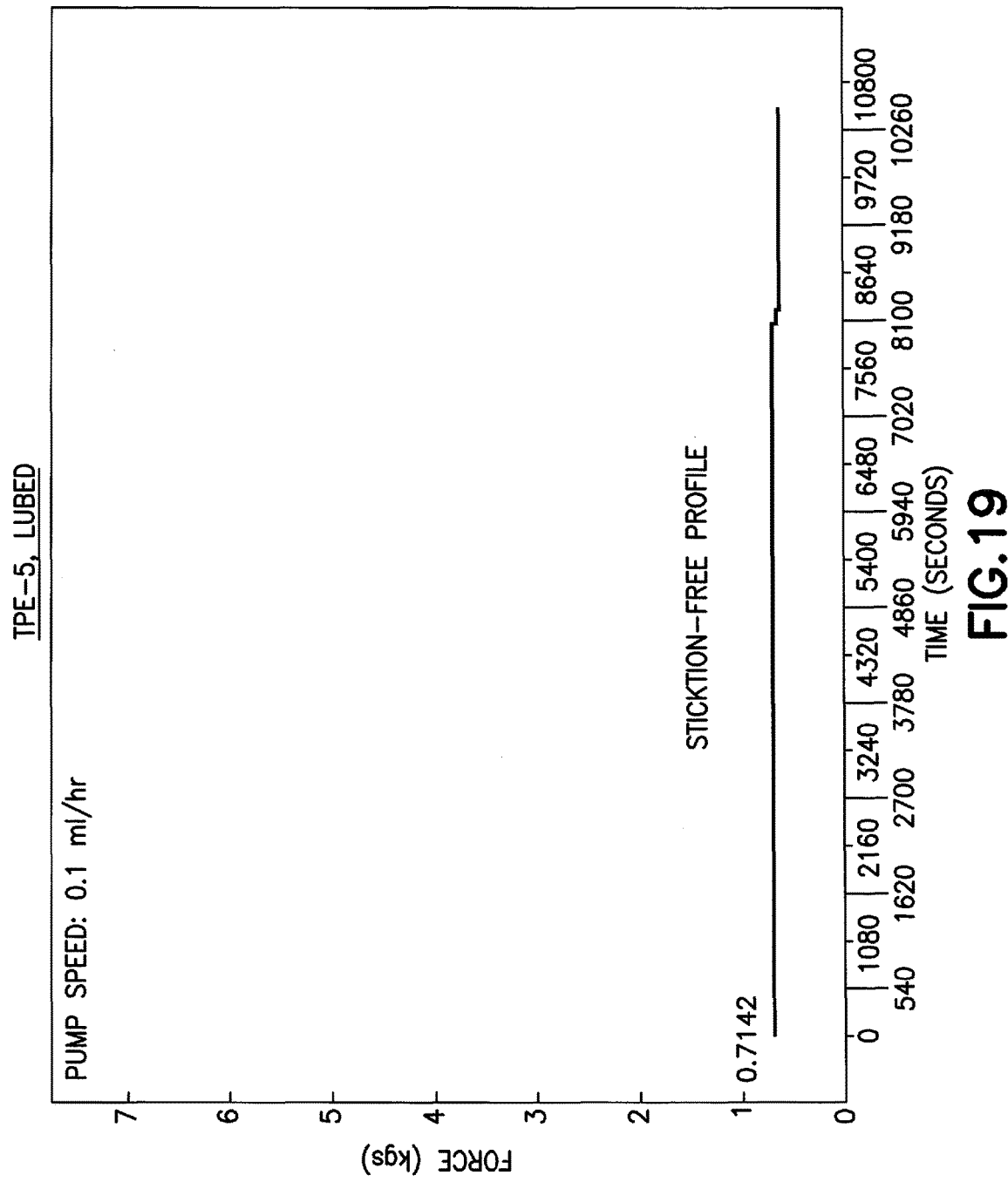
FIG. 19 is a graph of a pump force profile of a thermoplastic elastomer stopper in accordance with an embodiment of the present invention.

In one embodiment, a stopper of the present disclosure is formed of a TPE based on a polyethylene blended with styrenic block copolymer. In such an embodiment, the propensity of the polyethylene to the surface of the stopper and the surface energy of the stopper enables a non-lubricated stopper that has the required functional properties of a stopper without requiring an external surface of the stopper to be lubricated, thereby eliminating an extra step of lubricant application onto syringe stopper surface. In this manner, the negative consequences of the external lubricant application on a stopper are eliminated. For example, the lubrication step on a stopper requires cost in lubricants and lubing instruments, time, and energy to operate and perform the lubrication step, and the stopper must be removed from an automated assembly process to be assembled. The non-lubricated stopper of the present disclosure also provides a stopper which allows for a complete automation stopper assembly process. The lower surface energy of polyethylene (~35 mJ/m$^2$) compared to polystyrene 41 mJ/m$^2$) in a polyethylene and styrenic block copolymer blend can result into preferential segregation of polyethylene to the surface, reduced interaction between stopper and barrel material, and sticktion-free performance. This is also supported by an Atomic Force Microscopy (AFM) measurement on a TPE-2-S0.6 embodiment, where hard phase is preferentially segregated towards the surface. Since the hard phase of styrenic block copolymer is chemically linked to the soft phase, this suggests that polyethylene is preferentially segregated to the surface. To determine the critical concentration of polyethylene needed in a styrenic block copolymer, two TPE stopper formulations with polyethylene content of 8% (TPE-6) and 25% (TPE-2 with all slip agent level and TPE-5) were studied in a 10 ml embodiment with a polypropylene barrel and plunger rod. For example, the pump force profile for TPE-2-S0.6 and TPE-6 are given in FIGS. 18 and 19. Sticktion at 0.1 ml/hr pump speed was observed with the formulation with 8% polyethylene content but no sticktion in case of 25% polyethylene content, indicating that the critical polyethylene concentration exists in the 8% to 25% range.

The syringe stopper is constantly under stress in the syringe assembly and undergoes a compression set with time. Syringe functional performances, hand force and leak performance, are dependent on stopper dimension and are competing requirements. Syringe hand forces increase or become worse and pressure to leak increases or becomes better with an increase in stopper OD. Since a stopper OD is the highest just after assembly, the hand force is a worst case for just assembled syringes. In contrast, pressure to leak decreases or becomes worse with time. In one embodiment, the stopper design and dimensions are designed to achieve acceptable hand forces at T=0 but at the same time satisfy leak performance during the entire shelf life. A compression set measurement (ASTM D395-03, Method B, 25% strain for 22 hrs at 70 degrees C.) gives a good indication of the magnitude of stopper OD change with time. The leak performance for different TPE stopper embodiments, as shown in FIG. 20, suggests that the leakage performance was not met by the TPE formulations with compression set >50%. The formulations with acceptable leakage performance had a compression set ≤35%.

As discussed above, unlubed stoppers having a high TPE viscosity is not only helpful in the ability to have unlubed stoppers but also provides good control in the ability to dispense filled liquid from a syringe. The ability to dispense droplets of blood without any squirting or jetting is important for the use of a syringe in applications where blood droplets are placed on glass slides for analysis. Jetting of blood would result in the contamination of a work place during such practice and the possibility of infection to health care workers, which is not desirable. Additionally, such syringes can dispense small highly accurate increments of liquid repeatedly without sudden surges. Thus, a syringe assembly including a stopper of the present disclosure can be used to administer a medicament to a patient without the danger of surges whereby accurate control of dosage and greatly enhanced patient safety are realized.

Attaching a needle to a syringe creates back-pressure and improves the hand control. Thus, all of the tests, research, and experimentation of the present disclosure were conducted in the worst case of syringes without an attached needle. The test for the ability to control blood dispensing at droplet level was conducted in 10 ml and E-beam sterilized syringes using sheep blood as shown in FIG. 21. FIG. 21 also documents the viscosity at different shear rates measured using a capillary rheometer at 205° C. (Die: Round-hole 20 mm length/1 mm diameter/180 degree inlet, Piston: d=15 mm, and melting time=7 min). TPE-1-S0.6 and TPE-2 (with all slip agent level), with high formulation viscosity, exhibit good hand control but low viscosity. TPE-3 (polypropylene blended with styrenic block copolymer based) and TPE-5 (polyethylene blended with styrenic block copolymer) exhibit poor hand control with blood.

The amount of slip agent (such as but not limited to Erucamide, oleamide, and behenamide) present in the TPE formulation also impacts syringe hand control with different fill liquids. For example, the tests, research, and experimentation of the present disclosure include hand control tests for isopropanol dispensed at droplet level for polyethylene blended with styrenic block copolymer based TPE-2 with different levels of slip agent, Erucamide, in a 10 ml stopper (Design-5). A critical level of slip agent between 0.2-0.3% is needed for good syringe hand control. In the case of such formulation, stopper strain in assembled syringes should be optimized to eliminate any visual defect due to the preferential segregation of slip agent on the stopper surface. Such visual defect can give the perception of foreign matter to the end user. The presence of a slip agent in the formulation also decreases or improves the syringe forces without impacting the leak performance as syringe leak performance is primarily dependent on the interference between syringe components. FIG. 22 documents the force changes with different slip agent level TPE-2 stoppers in 10 ml Design-5 and E-beam sterilized syringes.

The TPE stopper in a syringe assembly undergoes complex compression and tensile modes during use and the TPE material property in both tensile and compression affects the syringe functional performance (hand force and leak performance). A stress-strain curve is a material property that characterizes the behavior of a particular material. The tests, research, and experimentation of the present disclosure include using FEA simulation to predict the desired stress at a given strain level that would result in the best functional performance. Referring to FIG. 11, the stress values for a desired curve for TPE-1-S0.6, TPE-2-S0.6, and TPE-3 are given. The tests, research, and experimentation of the present disclosure include using FEA simulation to assign relative ranking for syringe leakage pressure and sustaining force for these three TPE formulations (FIG. 23) and it matched with the experimental data (FIG. 24). The leak pressure and sustaining force test was conducted in 10 ml Design-4 in non-sterile condition (aged for 1 week at 60° C.). TPE-3 had the lowest or worst leak performance. Even though the sustaining force with TPE-1-S0.6 and TPE-2-S0.6 were higher than TPE-3, it was acceptable. Since leak performance becomes worse with time, TPE-1-S0.6, TPE-2-S0.3, and TPE-2-S0.6 can be selected as the final TPE formulation with no sticktion and acceptable syringe force and leak performance with the possibility to be used without externally applied silicone lube.

TPE stress at a given strain is also reflected by the hardness of the formulation. TPE1-S0.6 and TPE-2 (with 0.3% and 0.6% Erucamide level), which meet the stress at given strain requirement, have a hardness of 53 Shore A and 63 Shore A. Thus, the most preferred hardness range for a TPE stopper formulation of the present disclosure is 53-63 Shore A.

Based on the above presented data, the final TPE selection table for a syringe stopper is presented in FIG. 25. TPE-1-S0.6, TPE-2-S0.3, and TPE-2-S0.6 meet all the requirements for a syringe stopper application and can be used in an unlubed condition.

In the case of using a syringe with TPE stopper of a higher thermal expansion coefficient than the barrel material, accidental exposure at high temperatures (such as 60° C.) for prolonged time leads to barrel bulge. This is due to the increased stress on the barrel at high temperature due to the mismatch in thermal expansion coefficient leading to non-reversible creep of the barrel or bulging at a stopper parking position. The thermal expansion coefficient of a syringe stopper can be reduced by the addition of an inorganic filler such as silica or calcium carbonate due to the low thermal expansion coefficient of such inorganic fillers and their influence on the crystalline architecture of the TPE matrix. In this manner, the addition of inorganic filler compensates for the high coefficient of thermal expansion of a thermoplastic elastomer resulting into an acceptable creep level of barrel material.

An autoclavable syringe can also be obtained with the use of a high melting temperature polymer in formulation. Conventional autoclavable stoppers generally are formed of thermoset rubbers coated with a lubricant. However, manufacturing of such conventional autoclavable stoppers require multiple steps and generate a lot of waste. Conventionally, a thermoplastic elastomer stopper based on polypropylene blends can also be used in autoclavable syringes. The autoclavablitiy of such syringes is obtained by the addition of a lot of inorganic fillers into a stopper formulation to provide structural integrity at autoclaving temperatures. The use of inorganic fillers damages the surface of the mold resulting in reduced efficiency and high running costs. Also, the presence of inorganic fillers in the composition results in issues associated with extractables and leachables during use and storage of syringes. Therefore, there is a need for a thermoplastic elastomeric composition for the manufacturing of syringe stoppers which can be autoclaved without the need for inorganic fillers.

As discussed above, a stopper of the present disclosure is made of a material that provides the required functional properties of a stopper without requiring an external surface of the stopper to be lubricated. For example, a stopper of the present disclosure may be formed of a thermoplastic elastomer. In this manner, a stopper of the present disclosure also allows for an autoclavable stopper for a syringe assembly. In one embodiment, the thermoplastic elastomer composition of a stopper of the present disclosure is based on high melting temperature polymers. For example, a melting temperature ≥170 degrees C. is required for autoclavable syringes. As previously discussed, in one embodiment, a stopper of the present disclosure may be formed of a thermoplastic elastomer composition including a blend of injection moldable elastomers including block copolymers and a high transition temperature polymer. In some embodiments, the elastomer may include a styrene block copolymer, an olefin block copolymer, polyisoprene, and butyl rubber blended with the high transition temperature polymers which may include ethylene-tetrafluoro-ethylene (ETFE) and fluorinated ethylene propylene (FEP) polymers. In one embodiment, the composition of a stopper of the present disclosure may include 30 to 65% by weight of elastomers such as but not limited to styrene block copolymer and olefin block copolymer, 10 to 35% by weight of high transition temperature polymers such as but not limited to ethylene-tetrafluoro-ethylene, and 20-35% by weight of other additives such as mineral oil to meet the desired processing requirements and material properties such as hardness, tensile, viscosity, and compression set properties for a stopper for a syringe assembly application. In other embodiments, the composition of a stopper of the present disclosure contains a radiation stabilizer, an antioxidant, and/or a processing aid. A stopper of the present disclosure overcomes the deficiencies of conventional stoppers by providing an injection moldable thermoplastic syringe stopper wherein the sticktion free performance is generated by the migration to the surface of hydrocarbon liquids such as mineral oil incorporated in the composition of the stopper. The high temperature stable polymer at the level of at least 10 to 35% by weight in the composition provides structural integrity during autoclaving processes and any other exposure to high temperature conditions. For example, the high transition temperature polymers may include ethylene-tetrafluoro-ethylene (ETFE) and fluorinated ethylene propylene (FEP) polymers. As discussed above, the thermoplastic elastomer composition of a stopper of the present disclosure is based on high melting temperature polymers. For example, a melting temperature ≥170 degrees C. is required for autoclavable syringes. In this manner, a stopper of the present disclosure results in a lubricant free, sticktionless, autoclavable, and injection moldable stopper while eliminating the step of an external lubrication on a stopper.

Syringe assembly 10 may be used to fill syringe barrel 12 with a medication from a separate vial prior to use. For example, syringe assembly 10 may be used with non-preloaded medication kits such as a diabetes therapy kit.

Referring now to FIG. 1, the use of syringe assembly 10 to fill syringe barrel 12 with medication from a separate vial prior to use will now be described. With syringe assembly 10 in the position shown in FIG. 1 and with a needle assembly locked to distal end 32 of syringe barrel 12 and placed in communication with a vial containing fluid, when it is desired to aspirate or pull the fluid, such as a medication, into chamber 36 of syringe barrel 12, a user moves plunger rod 14 in a direction generally along arrow A until the desired amount of the fluid is pulled into chamber 36 of syringe barrel 12. In this manner, movement of stopper 16 via plunger rod 14 in the direction generally along arrow A creates a vacuum inside chamber 36 of syringe barrel 12. As the user moves stopper 16 via plunger rod 14 in a direction generally along arrow A, the user actively increases the volume within chamber 36 of syringe barrel 12. Because the stopper is sized relative to syringe barrel 12 to provide sealing engagement with the interior wall of syringe barrel 12, as described above, and because the needle assembly locked to distal end 32 of syringe barrel 12 is placed in a vial containing fluid, no air can enter into chamber 36 of syringe barrel 12 and, thus, the same number of air molecules are located within chamber 36 as the user actively increases the volume within chamber 36. This decreases the pressure in chamber 36 of syringe barrel 12 relative to the air pressure outside of syringe barrel 12. Therefore, a vacuum, i.e., a space of lower air pressure, is created to pull the fluid, such as a medication, into chamber 36 of syringe barrel 12.

Syringe assembly 10 may also be used in a pre-filled syringe assembly and/or an injectable syringe assembly. In this manner, the need for the user to fill the device prior to injection is eliminated, thereby saving time and maintaining consistent volumes for delivery. Syringe assembly 10 in a pre-filled syringe application may be provided for end use with a fluid, such as a medication, contained within chamber 36 of syringe barrel 12, pre-filled by the manufacturer. In this manner, syringe assembly 10 can be manufactured, pre-filled with a medication, sterilized, and packaged in appropriate packaging for delivery, storage, and use by the end user, without the need for the end user to fill the syringe with medication from a separate vial prior to use. In such an embodiment, syringe assembly 10 may include a cap or sealing member disposed at distal end 32 of syringe barrel 12 to seal a fluid, such as a medication, within chamber 36 of syringe barrel 12.

Referring to FIGS. 1 and 2A, the use of syringe assembly 10 to expel a fluid, such as a medication, contained within chamber 36 of syringe barrel 12 will now be described. In such an embodiment, a fluid is contained within chamber 36 of syringe barrel 12 and stopper 16 is positioned adjacent proximal end 34 of syringe barrel 12 as shown in FIG. 2A. In a pre-filled syringe application, a user may first remove a cap or sealing member from distal end 32 of syringe barrel 12. A user can then attach tip 42 of syringe barrel 12 to a separate needle assembly or IV connection assembly and lockingly engage the needle assembly or IV connection assembly to tip 42 of syringe barrel 12 in a known manner. Prior to dispensing any medication, any air trapped within chamber 36 of syringe barrel 12 can be expelled in a known manner.

When it is desired to expel or deliver the medication contained within syringe barrel 12, syringe assembly 10 is grasped with the user's thumb on flange 66 of plunger rod 14 and with the user's fingers extending around flange 40 of syringe barrel 12. In this manner, syringe assembly 10 is grasped by a user in a well known and well recognized manner. Next, the user effects a squeezing movement between the thumb on flange 66 of plunger rod 14 and four fingers grasping flange 40 of syringe barrel 12, thereby causing stopper 16 via plunger rod 14 to move in a direction generally along arrow B (FIG. 1). In this manner, movement of stopper 16 via plunger rod 14 in the direction generally along arrow B forces a fluid contained within chamber 36 of syringe barrel 12 to be forced out outlet opening 38. The fluid can be expelled from syringe barrel 12 through outlet opening 38 into a separate needle assembly or IV assembly and into the patient.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A stopper for a syringe assembly, the syringe assembly including a syringe barrel defining a chamber having an interior configured for receiving the stopper, the stopper formed of a composition comprising a non-lubricated thermoplastic elastomer, wherein the compression set of the thermoplastic elastomer is ≤50% when measured at 25% compression for 22 hrs at 70 degrees C. (ASTM D395-03, Method B), wherein the hardness of the thermoplastic elastomer is 40-70 Shore A (ASTM D2240-05), and wherein the viscosity of the thermoplastic elastomer, at 205 degrees C., is ≥70.0 Pa·s at 1,000 $s^{-1}$ shear rate, ≥12.0 Pa·s at 10,000 $s^{-1}$ shear rate, and ≥3.0 Pa·s at 50,000 $s^{-1}$ shear rate, wherein the stopper composition has a hard polymer phase having a high melt temperature >170 degrees C. and an elastomeric phase.

2. The stopper of claim 1, wherein the compression set of the thermoplastic elastomer is ≤35% when measured at 25% compression for 22 hrs at 70 degrees C.

3. The stopper of claim 1, wherein the compression set of the thermoplastic elastomer is 10%-35% when measured at 25% compression for 22 hrs at 70 degrees C.

4. The stopper of claim 1, wherein the hardness of the thermoplastic elastomer is 45-65 Shore A.

5. The stopper of claim 1, wherein the hardness of the thermoplastic elastomer is 53-63 Shore A.

6. The stopper of claim 1, wherein the viscosity of the thermoplastic elastomer is 70.0 Pa·s-320.0 Pa·s at 1,000 $s^{-1}$ shear rate.

7. The stopper of claim 1, wherein the viscosity of the thermoplastic elastomer is 100.0 Pa·s-170.0 Pa·s at 1,000 $s^{-1}$ shear rate.

8. The stopper of claim 1, wherein the viscosity of the thermoplastic elastomer is 12.0 Pa·s-46.0 Pa·s at 10,000 $s^{-1}$ shear rate.

9. The stopper of claim 1, wherein the viscosity of the thermoplastic elastomer is 16.0 Pa·s-27.0 Pa·s at 10,000 $s^{-1}$ shear rate.

10. The stopper of claim 1, wherein the viscosity of the thermoplastic elastomer is 3.0 Pa·s-12.0 Pa·s at 50,000 $s^{-1}$ shear rate.

11. The stopper of claim 1, wherein the viscosity of the thermoplastic elastomer is 4.5 Pa·s-7.5 Pa·s at 50,000 $s^{-1}$ shear rate.

12. A syringe assembly, comprising:
a syringe barrel having a proximal end, a distal end, and a sidewall extending therebetween and defining a chamber having an interior;
a stopper disposed within the interior of the syringe barrel, the stopper formed of a composition comprising a non-lubricated thermoplastic elastomer, wherein the compression set of the thermoplastic elastomer is ≤50% when measured at 25% compression for 22 hrs at 70 degrees C. (ASTM D395-03, Method B), wherein the hardness of the thermoplastic elastomer is 40-70 Shore A (ASTM D2240-05), and wherein the viscosity of the thermoplastic elastomer, at 205 degrees C., is ≥70.0 Pa·s at 1,000 $s^{-1}$ shear rate, ≥12.0 Pa·s at 10,000 $s^{-1}$ shear rate, and ≥3.0 Pa·s at 50,000 $s^{-1}$ shear rate, wherein the stopper composition has a hard polymer phase having a high melt temperature >170 degrees C. and an elastomeric phase; and a plunger rod having a first end engageable with a portion of the stopper.

13. The syringe assembly of claim 12, wherein the syringe barrel has a barrel material composition and the stopper has a stopper composition that is different than the barrel material composition.

14. The syringe assembly of claim 13, wherein the barrel material composition comprises polypropylene and the stopper composition does not comprise polypropylene.

15. The syringe assembly of claim 12, wherein the hard phase comprises at least one of ethylene-tetra-fluoro-ethylene and fluorinated ethylene propylene polymers.

16. A syringe assembly, comprising:
   a syringe barrel having a proximal end, a distal end, and a sidewall extending therebetween and defining a chamber having an interior, the syringe barrel having a barrel material composition;
   a stopper formed of a composition comprising a non-lubricated thermoplastic elastomer, wherein the compression set of the thermoplastic elastomer is ≤50% when measured at 25% compression for 22 hrs at 70 degrees C. (ASTM D395-03, Method B), wherein the hardness of the thermoplastic elastomer is 40-70 Shore A (ASTM D2240-05), and wherein the viscosity of the thermoplastic elastomer, at 205 degrees C., is ≥70.0 Pa·s at 1,000 $s^{-1}$ shear rate, ≥12.0 Pa·s at 10,000 $s^{-1}$ shear rate, and ≥3.0 Pa·s at 50,000 $s^{-1}$ shear rate, wherein the stopper composition has a hard polymer phase having a high melt temperature >170 degrees C. and an elastomeric phase, the stopper slidably disposed within the interior of the chamber of the syringe barrel, the stopper sized relative to the interior of the chamber of the syringe barrel to provide sealing engagement with the sidewall of the syringe barrel; and
   a plunger rod having a first end engageable with a portion of the stopper,
   wherein the composition of the stopper is different than the barrel material composition.

17. The stopper of claim 1, wherein the hard polymer phase is blended with the elastomeric phase.

18. The stopper of claim 17, wherein the hard polymer phase comprises at least one of ethylene-tetra-fluoro-ethylene and fluorinated ethylene propylene polymers and the elastomeric phase comprises at least one of a styrene block copolymer, an olefin block copolymer, SBR rubber, or polyisoprene.

19. The stopper of claim 1, wherein the syringe barrel has a barrel material composition and the stopper has a stopper composition that is different than the barrel material composition, and wherein the stopper composition does not contain more than 4% of the barrel material.

20. The stopper of claim 1, wherein the stopper has a first rib having a first contact area with respect to the syringe barrel and a second rib having a second contact area with respect to the syringe barrel, and wherein the first contact area is greater than the second contact area, and wherein pressure applied to the syringe barrel from the first contact area provides leakage resistance and the pressure applied by the second contact area provides a reduction of pump and break-loose forces.

21. The syringe assembly of claim 12, wherein the hard polymer phase is blended with the elastomeric phase.

22. The syringe assembly of claim 13, wherein the stopper composition does not contain more than 4% of the barrel material composition.

23. The syringe assembly of claim 16, wherein the stopper composition does not contain more than 4% of the barrel material composition.

* * * * *